US008008501B2

(12) United States Patent
Singh et al.

(10) Patent No.: US 8,008,501 B2
(45) Date of Patent: Aug. 30, 2011

(54) QUINOLINE COMPOUNDS AND THEIR USES

(75) Inventors: Rajinder Singh, Belmont, CA (US);
Hui Li, Millbrae, CA (US)

(73) Assignee: Rigel Pharmaceuticals, Inc., South San Francisco, CA (US)

( * ) Notice: Subject to any disclaimer, the term of this patent is extended or adjusted under 35 U.S.C. 154(b) by 1568 days.

(21) Appl. No.: 10/931,481

(22) Filed: Sep. 1, 2004

(65) Prior Publication Data
US 2005/0113412 A1 May 26, 2005

Related U.S. Application Data

(60) Provisional application No. 60/502,605, filed on Sep. 12, 2003.

(51) Int. Cl.
*C07D 215/38* (2006.01)
(52) U.S. Cl. ........................................ 546/157; 514/314
(58) Field of Classification Search .................. 546/157; 514/314
See application file for complete search history.

(56) References Cited

U.S. PATENT DOCUMENTS

| 4,087,535 A | 5/1978 | Heubach |
| 4,829,072 A | 5/1989 | Hamprecht et al. |

FOREIGN PATENT DOCUMENTS

| EP | 0 098 486 | 1/1984 |
| JP | 11-189586 | 7/1999 |
| WO | WO 94/24095 | 10/1994 |

OTHER PUBLICATIONS deWeck, abstract only of CA 142:480237, abstract of J of Invest allerg and Clin Immunol, vol. 14(4), pp. 253-273, 2004.*
Anthony R. West, Solid State Chemistry and its Application, Wiley, New York, 1988, pp. 358 &365.*
English translation of Anthony R West, Solid State Chemistry and its Application, Wiley, New York, 1988, pp. 358 & 365.*
West, Anthony R., "Solid State Chemistry and its Application", Wiley, New York, 1988, pp. 358 and 365.*
Display for Chemcats, Chemical Library, Answer 1, "4-Isoxazolecarobxylic acid, 5-methyl-3-phenyl-, 6-fluoro-2-methyl-4-quinolinyl ester", © 2004 ACS on STN, CAS Registry No. 216774-15-1,Order No. BTB 01297 (1 pg.), Supplier: Ambinter.
Display for Chemcats, Chemical Library, Answer 2, "6-fluoro-2-methyl-4-quinolyl 5-methyl-3-phenylisoxazole-4-carboxylate", © 2004 ACS on STN, CAS Registry No. 216774-15-1,Order No. BTB 01297 (2 pgs.), Supplier: Maybridge plc.

* cited by examiner

*Primary Examiner* — D M Seaman
(74) *Attorney, Agent, or Firm* — Travis Young; McDonnell Boehnen Hulbert & Berghoff LLP

(57) ABSTRACT

The present invention provides quinoline compounds that inhibit the IgE receptor signaling cascade that leads to the release of chemical mediators, intermediates and methods of synthesizing the compounds and methods of using the compounds in a variety of contexts, including in the treatment and prevention of diseases characterized by, caused by or associated with the release of chemical mediators via degranulation and other processes effected by activation of the IgE receptor signaling cascade.

23 Claims, 4 Drawing Sheets

QUINOLINE COMPOUNDS AND THEIR USES

1. CROSS REFERENCE TO RELATED APPLICATION

Figure 1:
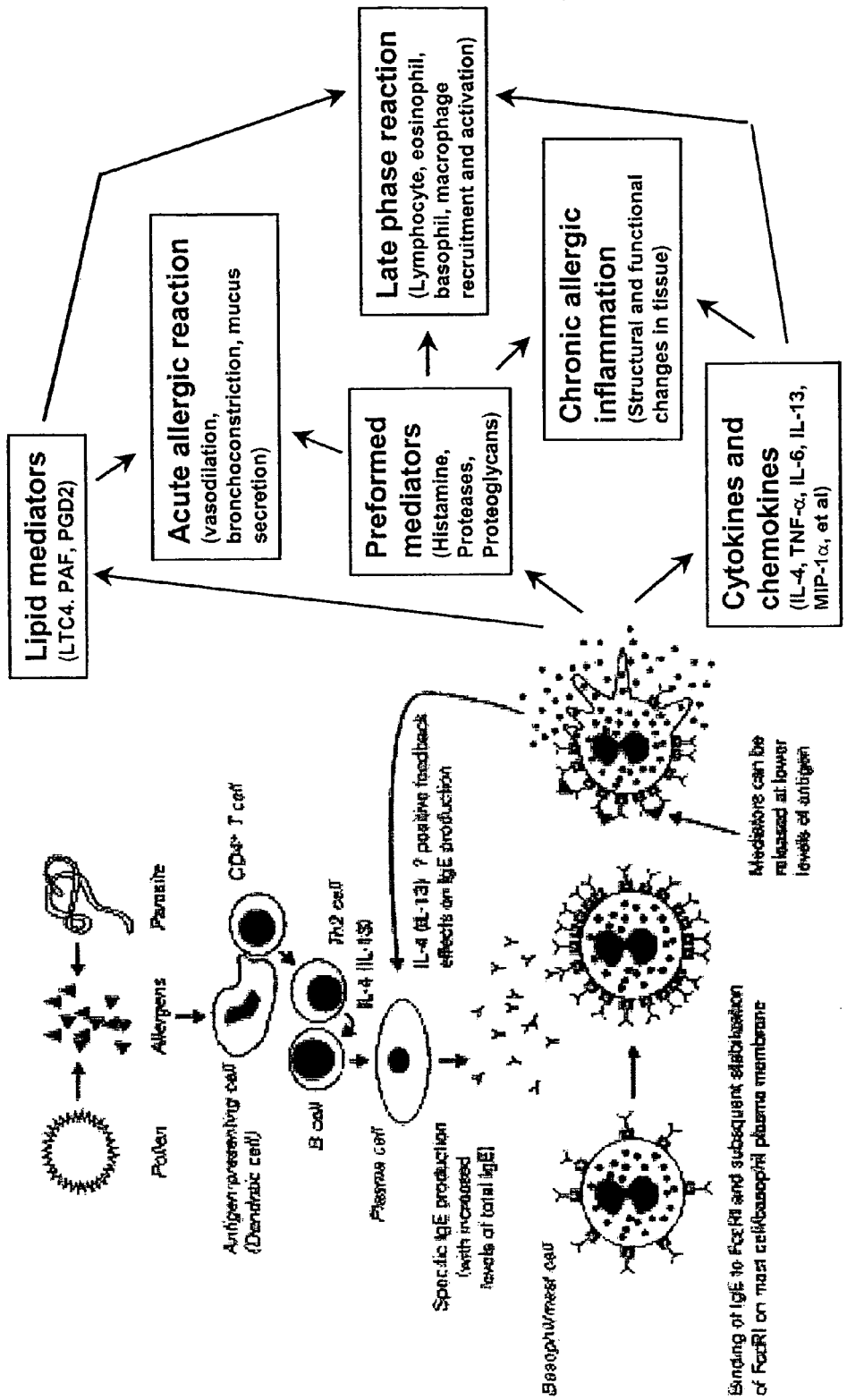

This application claims benefit under 35 U.S.C. §119(e) to application Ser. No. 60/502,605, filed Sep. 12, 2003, entitled "Quinoline Compounds and Their Uses".

2. FIELD OF THE INVENTION

The present invention relates generally to quinoline compounds, pharmaceutical compositions comprising the compounds, intermediates and synthetic methods of making the compounds and methods of using the compounds and compositions to, among other things, inhibit degranulation of mast and/or basophil cells in a variety of contexts.

3. BACKGROUND OF THE INVENTION

Crosslinking of allergen to receptor bound IgE activates a signaling cascade in mast and basophil cells that results in the release of chemical mediators responsible for numerous adverse events. For example, such crosslinking leads to the release of preformed mediators of Type I (immediate) anaphylactic hypersensitivity reactions, such as histamine, from storage sites in granules via degranulation. It also leads to the synthesis and release of other mediators, including leukotrienes, prostaglandins and platelet-activating factors (PAFs), that play important roles in inflammatory reactions. Other mediators that are synthesized and released upon allergen crosslinking include cytokines and nitric oxide.

As these mediators are responsible for, or play important roles in, the manifestation of numerous adverse events, the availability of compounds capable of inhibiting the signaling cascade(s) responsible for their release and/or synthesis would be highly desirable.

4. SUMMARY OF THE INVENTION

In one aspect, the present invention provides novel quinoline compounds that, among other things, inhibit degranulation of mast and/or basophil cells. The compounds generally comprise a quinoline "core" having the following structure and numbering convention:

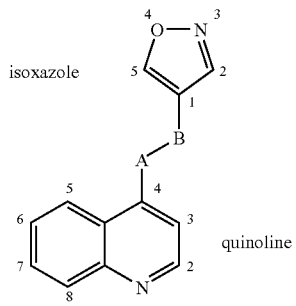

The compounds of the invention are substituted at the C4 carbon with a linking group "A-B". The quinoline portion can be further substituted at one or more positions (C2, C3, C5, C6, C7 and/or C8). The linking group tethers the quinoline portion of the compound to an isoxazole. The isoxazle can also be substituted, preferably with a methyl at the C5 carbon and preferably with a subsitutent at the C2 carbon of the isoxazole. The substituents at C2 and/or C5 of the isoxazole side chain, as well as the optional substituents at the other positions of the quinoline ring, may range broadly in character and physico-chemical properties. For example, the substituent(s) may be a branched, straight-chained or cyclic alkyl, a branched, straight-chained or cyclic heteroalkyl, a mono- or polycyclic aryl or a mono- or polycyclic heteroaryl. These substituent groups may be further substituted, as will be described in more detail below.

In another aspect, the present invention provides prodrugs of the quinoline compounds. Such prodrugs may be active in their prodrug form, or may be inactive until converted under physiological or other conditions of use to an active drug form. In the prodrugs of the invention, one or more functional groups of the quinoline compounds are included in promoieties that cleave from the molecule under the conditions of use, typically by way of hydrolysis, enzymatic cleavage or some other cleavage mechanism, to yield the functional groups. For example, primary or secondary amino groups may be included in an amide promoiety that cleaves under conditions of use to generate the primary or secondary amino group. Thus, the prodrugs of the invention include special types of protecting groups, termed "progroups," masking one or more functional groups of the quinoline compounds that cleave under the conditions of use to yield an active quinoline drug compound. Functional groups within the quinoline compounds that may be masked with progroups for inclusion in a promoiety include, but are not limited to, amines (primary and secondary), hydroxyls, sulfanyls (thiols), carboxyls, carbonyls, phenols, catechols, diols, alkynes, phosphates, etc. Myriad progroups suitable for masking such functional groups to yield promoieties that are cleavable under the desired conditions of use are known in the art. All of these progroups, alone or in combinations, may be included in the prodrugs of the invention. Specific examples of promoieties that yield primary or secondary amine groups that can be included in the prodrugs of the invention include, but are not limited to amides, carbamates, imines, ureas, phosphenyls, phosphoryls and sulfenyls. Specific examples of promoieties that yield sulfanyl groups that can be included in the prodrugs of the invention include, but are not limited to, thioethers, for example S-methyl derivatives (monothio, dithio, aminothio acetals), silyl thioethers, thioesters, thiocarbonates, thiocarbamates, asymmetrical disulfides, etc. Specific examples of promoieties that cleave to yield hydroxyl groups that can be included in the prodrugs of the invention include, but are not limited to, sulfonates, esters and carbonates. Specific examples of promoieties that yield carboxyl groups that can be included in the prodrugs of the invention included, but are not limited to, esters (including silyl esters, oxamic acid esters and thioesters), amides and hydrazides.

In one illustrative embodiment, the prodrugs of the invention are compounds according to structural formula (I) in which the protecting group of $R^c$ and $R^d$ is a progroup.

The quinoline compounds of the invention are potent inhibitors of mast and/or basophil cell degranulation. Thus, in still another aspect, the present invention provides methods of regulating, and in particular inhibiting, degranulation of mast and/or basophil cells. The method generally involves contacting a mast and/or basophil cell with an amount of a quinoline compound or prodrug of the invention, or an acceptable salt, hydrate, solvate, N-oxide and/or composition thereof, effective to regulate or inhibit degranulation of the cell. The method may be practiced in in vitro contexts or in in vivo contexts as a therapeutic approach towards the treatment or prevention of diseases characterized by, caused by or associated with mast and/or basophil cell degranulation.

While not intending to be bound by any theory of operation, it is believed that the quinoline compounds of the invention exert their inhibitory effect by blocking the IgE receptor signaling cascade initiated when the IgE receptor-bound IgE is cross-linked by antigen. Thus, the present invention also provides methods of regulating, and in particular inhibiting, the IgE receptor (also known as FcεR1) signaling cascade that leads to mast and/or basophil cell degranulation (IgE receptor-mediated degranulation). The methods also permit the regulation of, and in particular the inhibition of, downstream processes that result as a consequence of activating the IgE receptor signaling cascade. Such downstream processes include, but are not limited to, IgE-induced degranulation, cytokine production and/or release and/or the production and/or release of lipid mediators such as leukotrienes and prostaglandins. The method generally involves contacting a mast and/or basophil cell with an amount of a quinoline compound or prodrug of the invention, or an acceptable salt, hydrate, solvent, N-oxide and/or composition thereof, effective to regulate or inhibit the IgE receptor signaling cascade and/or a downstream process effected by the activation of this signaling cascade. The method may be practiced in in vitro contexts or in in vivo contexts as a therapeutic approach towards the treatment or prevention of diseases characterized by, caused by or associated with the IgE receptor signaling cascade, such as diseases effected by the release of granule specific chemical mediators upon degranulation, the release and/or synthesis of cytokines and/or the release and/or synthesis of lipid mediators such as leukotrienes and prostaglandins.

In yet another aspect, the present invention provides methods of treating and/or preventing diseases characterized by, caused by or associated with the release of chemical mediators as a consequence of activating the IgE receptor signaling cascade. The methods may be practiced in animals in veterinary contexts or in humans. The methods generally involve administering to an animal subject or human an amount of a quinoline compound or prodrug of the invention, or an acceptable salt, hydrate, solvate, N-oxide and/or composition thereof, effective to treat or prevent the disease. As discussed previously, activation of the IgE receptor signaling cascade leads to the release and/or synthesis of a variety of chemical substances that are pharmacological mediators of a wide variety of diseases. Any of these diseases may be treated or prevented according to the methods of the invention.

For example, in mast cells and basophil cells, activation of the IgE receptor signaling cascade leads to the immediate (i.e., within 1-3 min. of IgE receptor activation) release of preformed mediators of atopic and/or Type I hypersensitivity reactions (e.g., histamine, proteases such as tryptase, etc.) via the degranulation process. Such atopic or Type I hypersensitivity reactions include, but are not limited to, anaphylactic reactions to environmental and other allergens (e.g., pollens, insect and/or animal venoms, foods, drugs, etc.), hay fever, allergic conjunctivitis, allergic rhinitis, allergic asthma, atopic dermatitis, eczema, urticaria and certain gastrointestinal disorders.

The immediate release of the preformed mediators via degranulation is followed by the release and/or synthesis of a variety of other chemical mediators, including, among other things, platelet activating factor (PAF), prostaglandins and leukotrienes (e.g., LTC4) and the de novo synthesis and release of cytokines such as TNFα, IL-4, IL-5, IL-6, IL-13, etc. The first of these two processes occurs approximately 3-30 min. following IgE receptor activation; the latter approximately 30 min.-7 hrs. following receptor activation. These "late stage" mediators are thought to be in part responsible for the chronic symptoms of the above-listed atopic and Type I hypersensitivity reactions, and in addition are chemical mediators of rheumatoid arthritis, inflammation and inflammatory diseases (e.g., inflammatory bowel disease, ulcerative colitis, Crohn's disease, idiopathic inflammatory bowel disease, irritable bowel, spastic colon, etc.), low grade scarring (e.g., scleroderma, increased fibrosis, keloids, post-surgical scars, pulmonary fibrosis, vascular spasms, migraine, repurfusion injury and post myocardial infarction), certain autoimmune diseases (e.g., lupus, insulin-dependent diabetes, rheumatoid arthritis, multiple sclerosis, etc.) and sicca complex or syndrome. All of these diseases may be treated or prevented according to the methods of the invention.

Additional diseases which can be treated or prevented according to the methods of the invention include diseases associated with basophil cell and/or mast cell pathology. Examples of such diseases include, but are not limited to, diseases of the skin such as scleroderma, cardiac diseases such as post myocardial infarction, pulmonary diseases such as pulmonary muscle changes or remodeling and chronic obstructive pulmonary disease (COPD) and diseases of the gut such as inflammatory bowel syndrome (spastic colon).

5. BRIEF DESCRIPTION OF THE FIGURES

Figure 2:
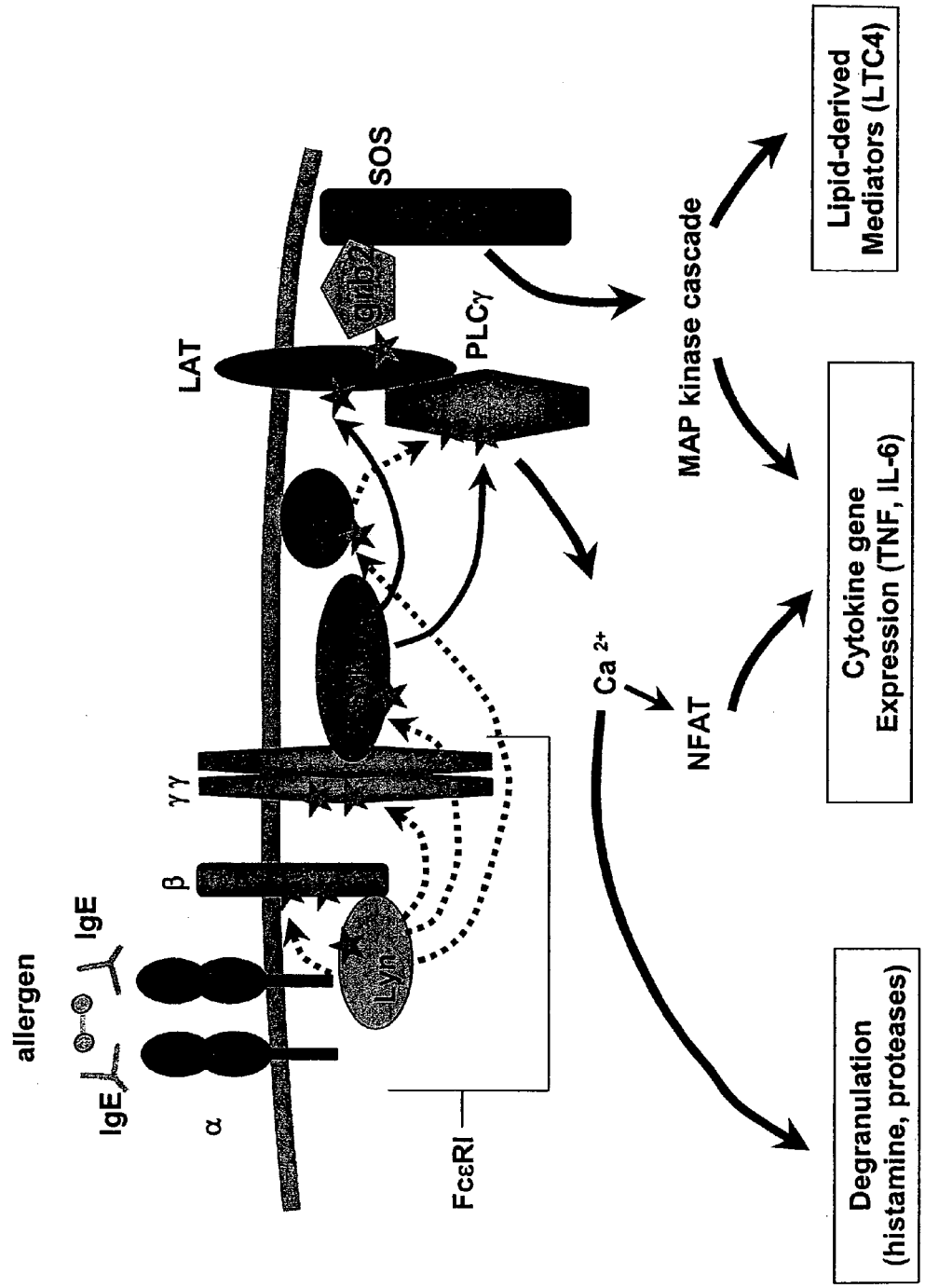
Figure 3:
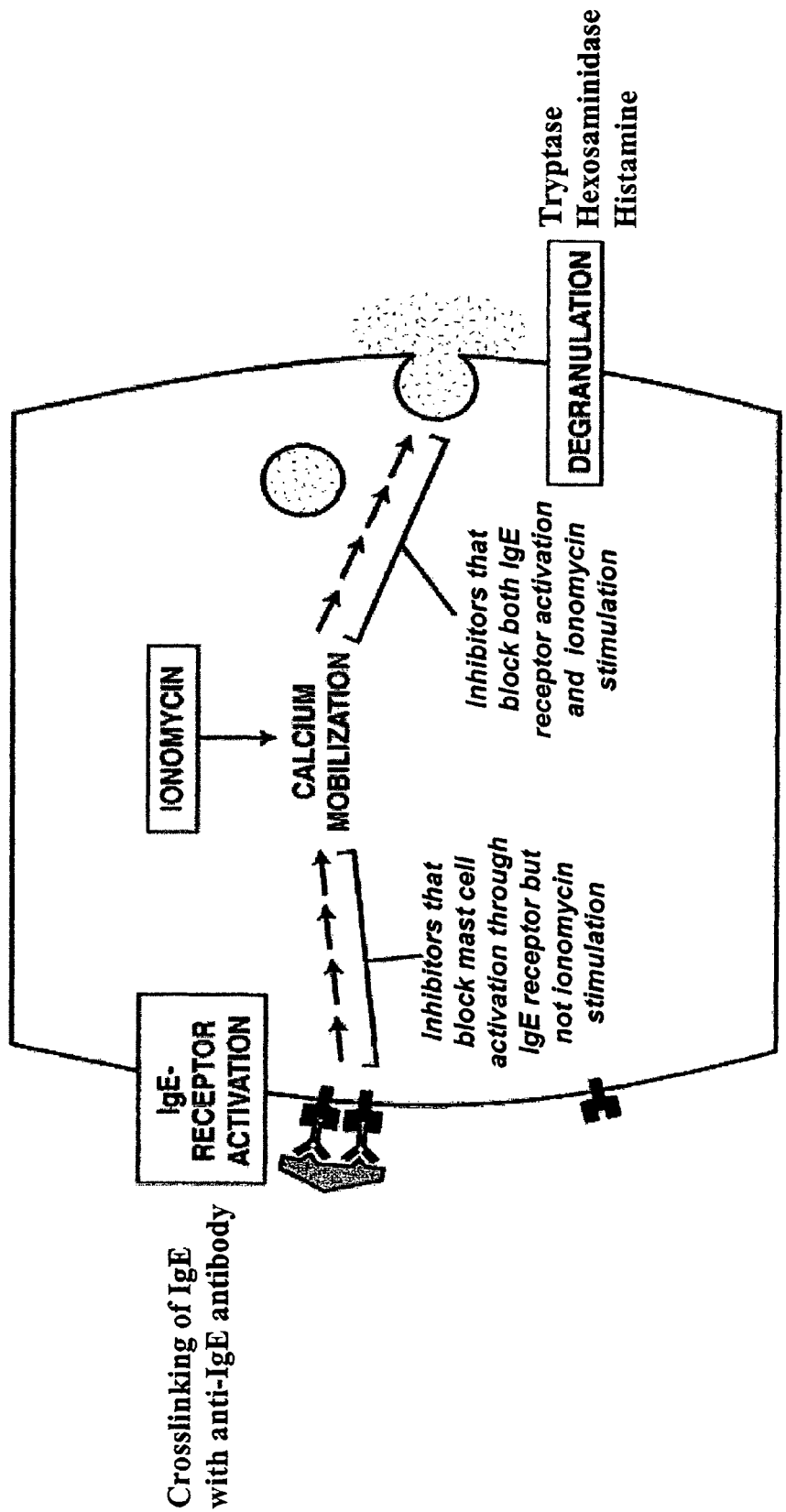
Figure 4:
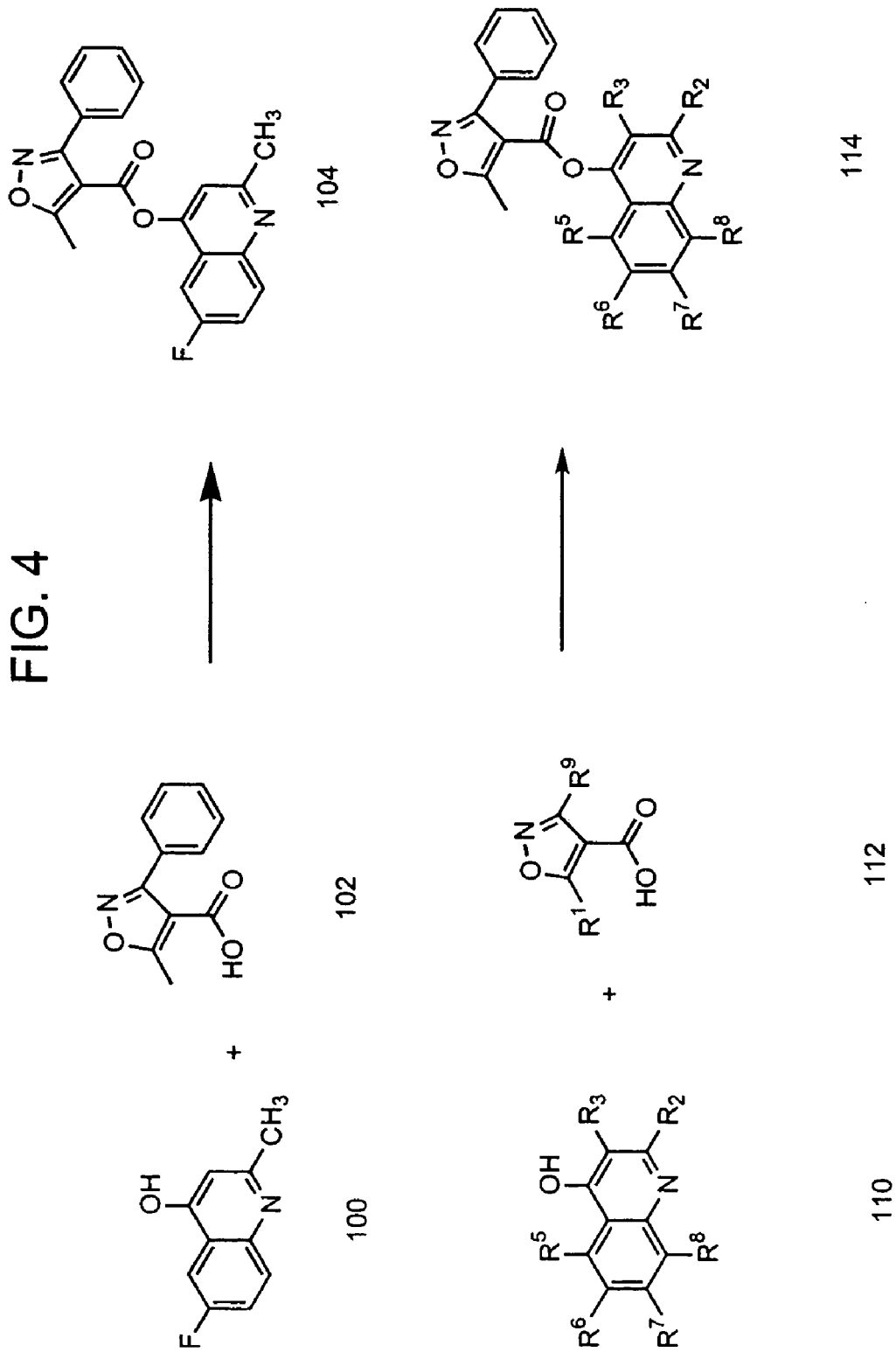

FIG. 1 provides a cartoon illustrating allergen-induced production of IgE and consequent release of preformed and other chemical mediators from mast cells;

FIG. 2 provides a cartoon illustrating the FCεR1 (IgE receptor) signal transduction cascade leading to degranulation of mast and/or basophil cells;

FIG. 3 provides a cartoon illustrating the putative points of action of compounds that selectively inhibit upstream IgE receptor-mediated (IgE-induced) degranulation and compounds that inhibit both IgE-induced and ionomycin-induced degranulation; and FIG. 4 depicts exemplary syntheses of compounds of the invention.

6. DETAILED DESCRIPTION OF THE PREFERRED EMBODIMENTS 6.1 Definitions

As used herein, the following terms are intended to have the following meanings:

"Alkyl" by itself or as part of another substituent refers to a saturated or unsaturated branched, straight-chain or cyclic monovalent hydrocarbon radical having the stated number of carbon atoms (i.e., C1-C6 means one to six carbon atoms) that is derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl, cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like. Where specific levels of saturation are intended, the nomenclature "alkanyl," "alkenyl" and/or "alkynyl" is used, as defined below. In preferred embodiments, the alkyl groups are (C1-C6) alkyl.

"Alkanyl" by itself or as part of another substituent refers to a saturated branched, straight-chain or cyclic alkyl derived by the removal of one hydrogen atom from a single carbon atom of a parent alkane. Typical alkanyl groups include, but are not limited to, methanyl; ethanyl; propanyls such as propan-1-yl, propan-2-yl (isopropyl), cyclopropan-1-yl, etc.; butanyls such as butan-1-yl, butan-2-yl (sec-butyl), 2-methyl-propan-1-yl (isobutyl), 2-methyl-propan-2-yl (t-butyl), cyclobutan-1-yl, etc.; and the like. In preferred embodiments, the alkanyl groups are (C1-C6) alkanyl.

"Alkenyl" by itself or as part of another substituent refers to an unsaturated branched, straight-chain or cyclic alkyl having at least one carbon-carbon double bond derived by the removal of one hydrogen atom from a single carbon atom of a parent alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl, prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like. In preferred embodiments, the alkenyl group is (C2-C6) alkenyl.

"Alkynyl" by itself or as part of another substituent refers to an unsaturated branched, straight-chain or cyclic alkyl having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like. In preferred embodiments, the alkynyl group is (C2-C6) alkynyl.

"Alkyldiyl" by itself or as part of another substituent refers to a saturated or unsaturated, branched, straight-chain or cyclic divalent hydrocarbon group having the stated number of carbon atoms (i.e., C1-C6 means from one to six carbon atoms) derived by the removal of one hydrogen atom from each of two different carbon atoms of a parent alkane, alkene or alkyne, or by the removal of two hydrogen atoms from a single carbon atom of a parent alkane, alkene or alkyne. The two monovalent radical centers or each valency of the divalent radical center can form bonds with the same or different atoms. Typical alkyldiyl groups include, but are not limited to, methandiyl; ethyldiyls such as ethan-1,1-diyl, ethan-1,2-diyl, ethen-1,1-diyl, ethen-1,2-diyl; propyldiyls such as propan-1,1-diyl, propan-1,2-diyl, propan-2,2-diyl, propan-1,3-diyl, cyclopropan-1,1-diyl, cyclopropan-1,2-diyl, prop-1-en-1,1-diyl, prop-1-en-1,2-diyl, prop-2-en-1,2-diyl, prop-1-en-1,3-diyl, cycloprop-1-en-1,2-diyl, cycloprop-2-en-1,2-diyl, cycloprop-2-en-1,1-diyl, prop-1-yn-1,3-diyl, etc.; butyldiyls such as, butan-1,1-diyl, butan-1,2-diyl, butan-1,3-diyl, butan-1,4-diyl, butan-2,2-diyl, 2-methyl-propan-1,1-diyl, 2-methyl-propan-1,2-diyl, cyclobutan-1,1-diyl; cyclobutan-1,2-diyl, cyclobutan-1,3-diyl, but-1-en-1,1-diyl, but-1-en-1,2-diyl, but-1-en-1,3-diyl, but-1-en-1,4-diyl, 2-methyl-prop-1-en-1,1-diyl, 2-methanylidene-propan-1,1-diyl, buta-1,3-dien-1,1-diyl, buta-1,3-dien-1,2-diyl, buta-1,3-dien-1,3-diyl, buta-1,3-dien-1,4-diyl, cyclobut-1-en-1,2-diyl, cyclobut-1-en-1,3-diyl, cyclobut-2-en-1,2-diyl, cyclobuta-1,3-dien-1,2-diyl, cyclobuta-1,3-dien-1,3-diyl, but-1-yn-1,3-diyl, but-1-yn-1,4-diyl, buta-1,3-diyn-1,4-diyl, etc.; and the like. Where specific levels of saturation are intended, the nomenclature alkanyldiyl, alkenyldiyl and/or alkynyldiyl is used. Where it is specifically intended that the two valencies are on the same carbon atom, the nomenclature "alkylidene" is used. In preferred embodiments, the alkyldiyl group is (C1-C6) alkyldiyl.

Also preferred are saturated acyclic alkanyldiyl groups in which the radical centers are at the terminal carbons, e.g., methandiyl (methano); ethan-1,2-diyl (ethano); propan-1,3-diyl (propano); butan-1,4-diyl (butano); and the like (also referred to as alkylenos, defined infra).

"Alkyleno" by itself or as part of another substituent refers to a straight-chain saturated or unsaturated alkyldiyl group having two terminal monovalent radical centers derived by the removal of one hydrogen atom from each of the two terminal carbon atoms of straight-chain parent alkane, alkene or alkyne. The locant of a double bond or triple bond, if present, in a particular alkyleno is indicated in square brackets. Typical alkyleno groups include, but are not limited to, methano; ethylenos such as ethano, etheno, ethyno; propylenos such as propano, prop[1]eno, propa[1,2]dieno, prop[1]yno, etc.; butylenos such as butano, but[1]eno, but[2]eno, buta[1,3]dieno, but[1]yno, but[2]yno, buta[1,3]diyno, etc.; and the like. Where specific levels of saturation are intended, the nomenclature alkano, alkeno and/or alkyno is used. In preferred embodiments, the alkyleno group is (C1-C6) or (C1-C3) alkyleno. Also preferred are straight-chain saturated alkano groups, e.g., methano, ethano, propano, butano, and the like.

"Heteroalkyl," Heteroalkanyl," Heteroalkenyl," Heteroalkynyl," Heteroalkyldiyl" and "Heteroalkyleno" by themselves or as part of another substituent refer to alkyl, alkanyl, alkenyl, alkynyl, alkyldiyl and alkyleno groups, respectively, in which one or more of the carbon atoms are each independently replaced with the same or different heteroatoms or heteroatomic groups. Typical heteroatoms and/or heteroatomic groups which can replace the carbon atoms include, but are not limited to, —O—, —S—, —S—O—, —NR'—, —PH—, —S(O)—, —S(O)$_2$—, —S(O)NR'—, —S(O)$_2$NR'—, and the like, including combinations thereof, where each R' is independently hydrogen or (C1-C6) alkyl.

"Cycloalkyl" and "Heterocycloalkyl" by themselves or as part of another substituent refer to cyclic versions of "alkyl" and "heteroalkyl" groups, respectively. For heteroalkyl groups, a heteroatom can occupy the position that is attached to the remainder of the molecule. Typical cycloalkyl groups include, but are not limited to, cyclopropyl; cyclobutyls such as cyclobutanyl and cyclobutenyl; cyclopentyls such as cyclopentanyl and cyclopentenyl; cyclohexyls such as cyclohexanyl and cyclohexenyl; and the like. Typical heterocycloalkyl groups include, but are not limited to, tetrahydrofuranyl (e.g., tetrahydrofuran-2-yl, tetrahydrofuran-3-yl, etc.), piperidinyl (e.g., piperidin-1-yl, piperidin-2-yl, etc.), morpholinyl (e.g., morpholin-3-yl, morpholin-4-yl, etc.), piperazinyl (e.g., piperazin-1-yl, piperazin-2-yl, etc.), and the like.

"Acyclic Heteroatomic Bridge" refers to a divalent bridge in which the backbone atoms are exclusively heteroatoms and/or heteroatomic groups. Typical acyclic heteroatomic bridges include, but are not limited to, —O—, —S—, —S—O—, —NR'—, —PH—, —S(O)—, —S(O)$_2$—, —S(O)NR'—, —S(O)$_2$NR'—, and the like, including combinations thereof, where each R' is independently hydrogen or (C1-C6) alkyl.

"Parent Aromatic Ring System" refers to an unsaturated cyclic or polycyclic ring system having a conjugated π electron system. Specifically included within the definition of "parent aromatic ring system" are fused ring systems in which one or more of the rings are aromatic and one or more of the rings are saturated or unsaturated, such as, for example, fluorene, indane, indene, phenalene, tetrahydronaphthalene, etc. Typical parent aromatic ring systems include, but are not limited to, aceanthrylene, acenaphthylene, acephenanthrylene, anthracene, azulene, benzene, chrysene, coronene, fluoranthene, fluorene, hexacene, hexaphene, hexalene, indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, tetrahydronaphthalene, triphenylene, trinaphthalene, and the like, as well as the various hydro isomers thereof.

"Aryl" by itself or as part of another substituent refers to a monovalent aromatic hydrocarbon group having the stated number of carbon atoms (i.e., C5-C15 means from 5 to 15 carbon atoms) derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like, as well as the various hydro isomers thereof. In preferred embodiments, the aryl group is (C5-C15) aryl, with (C5-C10) being even more preferred. Particularly preferred aryls are cyclopentadienyl, phenyl and naphthyl.

"Arylaryl" by itself or as part of another substituent refers to a monovalent hydrocarbon group derived by the removal of one hydrogen atom from a single carbon atom of a ring system in which two or more identical or non-identical parent aromatic ring systems are joined directly together by a single bond, where the number of such direct ring junctions is one less than the number of parent aromatic ring systems involved. Typical arylaryl groups include, but are not limited to, biphenyl, triphenyl, phenyl-naphthyl, binaphthyl, biphenyl-naphthyl, and the like. Where the number of carbon atoms in an arylaryl group are specified, the numbers refer to the carbon atoms comprising each parent aromatic ring. For example, (C5-C15) arylaryl is an arylaryl group in which each aromatic ring comprises from 5 to 15 carbons, e.g., biphenyl, triphenyl, binaphthyl, phenylnaphthyl, etc. Preferably, each parent aromatic ring system of an arylaryl group is independently a (C5-C15) aromatic, more preferably a (C5-C10) aromatic. Also preferred are arylaryl groups in which all of the parent aromatic ring systems are identical, e.g., biphenyl, triphenyl, binaphthyl, trinaphthyl, etc.

"Biaryl" by itself or as part of another substituent refers to an arylaryl group having two identical parent aromatic systems joined directly together by a single bond. Typical biaryl groups include, but are not limited to, biphenyl, binaphthyl, bianthracyl, and the like. Preferably, the aromatic ring systems are (C5-C15) aromatic rings, more preferably (C5-C10) aromatic rings. A particularly preferred biaryl group is biphenyl.

"Arylalkyl" by itself or as part of another substituent refers to an acyclic alkyl group in which one of the hydrogen atoms bonded to a carbon atom, typically a terminal or $sp^3$ carbon atom, is replaced with an aryl group. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylakenyl and/or arylalkynyl is used. In preferred embodiments, the arylalkyl group is (C6-C21) arylalkyl, e.g., the alkanyl, alkenyl or alkynyl moiety of the arylalkyl group is (C1-C6) and the aryl moiety is (C5-C15). In particularly preferred embodiments the arylalkyl group is (C6-C13), e.g., the alkanyl, alkenyl or alkynyl moiety of the arylalkyl group is (C1-C3) and the aryl moiety is (C5-C10).

"Parent Heteroaromatic Ring System" refers to a parent aromatic ring system in which one or more carbon atoms are each independently replaced with the same or different heteroatoms or heteroatomic groups. Typical heteroatoms or heteroatomic groups to replace the carbon atoms include, but are not limited to, N, NH, P, O, S, S(O), S(O)$_2$, Si, etc. Specifically included within the definition of "parent heteroaromatic ring systems" are fused ring systems in which one or more of the rings are aromatic and one or more of the rings are saturated or unsaturated, such as, for example, benzodioxan, benzofuran, chromane, chromene, indole, indoline, xanthene, etc. Also included in the definition of "parent heteroaromatic ring system" are those recognized rings that include substituents, such as benzopyrone. Typical parent heteroaromatic ring systems include, but are not limited to, acridine, benzimidazole, benzisoxazole, benzodioxan, benzodioxole, benzofuran, benzopyrone, benzothiadiazole, benzothiazole, benzotriazole, benzoxaxine, benzoxazole, benzoxazoline, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like.

"Heteroaryl" by itself or as part of another substituent refers to a monovalent heteroaromatic group having the stated number of ring atoms (e.g., "5-14 membered" means from 5 to 14 ring atoms) derived by the removal of one hydrogen atom from a single atom of a parent heteroaromatic ring system. Typical heteroaryl groups include, but are not limited to, groups derived from acridine, benzimidazole, benzisoxazole, benzodioxan, benzodiaxole, benzofuran, benzopyrone, benzothiadiazole, benzothiazole, benzotriazole, benzoxazine, benzoxazole, benzoxazoline, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like, as well as the various hydro isomers thereof. In preferred embodiments, the heteroaryl group is a 5-14 membered heteroaryl, with 5-10 membered heteroaryl being particularly preferred.

"Heteroaryl-Heteroaryl" by itself or as part of another substituent refers to a monovalent heteroaromatic group derived by the removal of one hydrogen atom from a single atom of a ring system in which two or more identical or non-identical parent heteroaromatic ring systems are joined directly together by a single bond, where the number of such direct ring junctions is one less than the number of parent heteroaromatic ring systems involved. Typical heteroaryl-heteroaryl groups include, but are not limited to, bipyridyl, tripyridyl, pyridylpurinyl, bipurinyl, etc. Where the number of atoms are specified, the numbers refer to the number of atoms comprising each parent heteroaromatic ring systems. For example, 5-15 membered heteroaryl-heteroaryl is a heteroaryl-heteroaryl group in which each parent heteroaromatic ring system comprises from 5 to 15 atoms, e.g., bipyridyl, tripuridyl, etc. Preferably, each parent heteroaromatic ring system is independently a 5-15 membered heteroaromatic, more preferably a 5-10 membered heteroaromatic. Also preferred are heteroaryl-heteroaryl groups in which all of the parent heteroaromatic ring systems are identical.

"Biheteroaryl" by itself or as part of another substituent refers to a heteroaryl-heteroaryl group having two identical parent heteroaromatic ring systems joined directly together by a single bond. Typical biheteroaryl groups include, but are not limited to, bipyridyl, bipurinyl, biquinolinyl, and the like. Preferably, the heteroaromatic ring systems are 5-15 membered heteroaromatic rings, more preferably 5-10 membered heteroaromatic rings.

"Heteroarylalkyl" by itself or as part of another substituent refers to an acyclic alkyl group in which one of the hydrogen atoms bonded to a carbon atom, typically a terminal or $sp^3$ carbon atom, is replaced with a heteroaryl group. Where specific alkyl moieties are intended, the nomenclature heteroarylalkanyl, heteroarylakenyl and/or heteroarylalkynyl is used. In preferred embodiments, the heteroarylalkyl group is a 6-21 membered heteroarylalkyl, e.g., the alkanyl, alkenyl or alkynyl moiety of the heteroarylalkyl is (C1-C6) alkyl and the heteroaryl moiety is a 5-15-membered heteroaryl. In particularly preferred embodiments, the heteroarylalkyl is a 6-13 membered heteroarylalkyl, e.g., the alkanyl, alkenyl or alkynyl moiety is (C1-C3) alkyl and the heteroaryl moiety is a 5-10 membered heteroaryl.

"Halogen" or "Halo" by themselves or as part of another substituent, unless otherwise stated, refer to fluoro, chloro, bromo and iodo.

"Haloalkyl" by itself or as part of another substituent refers to an alkyl group in which one or more of the hydrogen atoms is replaced with a halogen. Thus, the term "haloalkyl" is meant to include monohaloalkyls, dihaloalkyls, trihaloalkyls, etc. up to perhaloalkyls. For example, the expression "(C1-C2) haloalkyl" includes 1-fluoromethyl, difluoromethyl, trifluoromethyl, 1-fluoroethyl, 1,1-difluoroethyl, 1,2-difluoroethyl, 1,1,1-trifluoroethyl, perfluoroethyl, etc.

The above-defined groups may include prefixes and/or suffixes that are commonly used in the art to create additional well-recognized substituent groups. As examples, "alkyloxy" or "alkoxy" refers to a group of the formula —OR", "alkylamine" refers to a group of the formula —NHR" and "dialkylamine" refers to a group of the formula —NR"R", where each R" is independently an alkyl. As another example, "haloalkoxy" or "haloalkyloxy" refers to a group of the formula —OR'", where R'" is a haloalkyl.

"Protecting group" refers to a group of atoms that, when attached to a reactive functional group in a molecule, mask, reduce or prevent the reactivity of the functional group. Typically, a protecting group may be selectively removed as desired during the course of a synthesis. Examples of protecting groups can be found in Greene and Wuts, *Protective Groups in Organic Chemistry*, $3^{rd}$ Ed., 1999, John Wiley & Sons, NY and Harrison et al., *Compendium of Synthetic Organic Methods*, Vols. 1-8, 1971-1996, John Wiley & Sons, NY. Representative amino protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("SES"), trityl and substituted trityl groups, allyloxycarbonyl, 9-fluorenylmethyloxycarbonyl ("FMOC"), nitro-veratryloxycarbonyl ("NVOC") and the like. Representative hydroxylprotecting groups include, but are not limited to, those where the hydroxyl group is either acylated (e.g., methyl and ethyl esters, acetate or propionate groups or glycol esters) or alkylated such as benzyl and trityl ethers, as well as alkyl ethers, tetrahydropyranyl ethers, trialkylsilyl ethers (e.g., TMS or TIPPS groups) and allyl ethers.

"Prodrug" refers to a derivative of an active quinoline compound (drug) that requires a transformation under the conditions of use, such as within the body, to release the active quinoline drug. Prodrugs are frequently, but not necessarily, pharmacologically inactive until converted into the active drug. Prodrugs are typically obtained by masking a functional group in the quinoline drug believed to be in part required for activity with a progroup (defined below) to form a promoiety which undergoes a transformation, such as cleavage, under the specified conditions of use to release the functional group, and hence the active quinoline drug. The cleavage of the promoiety may proceed spontaneously, such as by way of a hydrolysis reaction, or it may be catalyzed or induced by another agent, such as by an enzyme, by light, by acid, or by a change of or exposure to a physical or environmental parameter, such as a change of temperature. The agent may be endogenous to the conditions of use, such as an enzyme present in the cells to which the prodrug is administered or the acidic conditions of the stomach, or it may be supplied exogenously.

A wide variety of progroups, as well as the resultant promoieties, suitable for masking functional groups in the active quinolines compounds to yield prodrugs are well-known in the art. For example, a hydroxyl functional group may be masked as a sulfonate, ester or carbonate promoiety, which may be hydrolyzed in vivo to provide the hydroxyl group. An amino functional group may be masked as an amide, carbamate, imine, urea, phosphenyl, phosphoryl or sulfenyl promoiety, which may be hydrolyzed in vivo to provide the amino group. A carboxyl group may be masked as an ester (including silyl esters and thioesters), amide or hydrazide promoiety, which may be hydrolyzed in vivo to provide the carboxyl group. Other specific examples of suitable progroups and their respective promoieties will be apparent to those of skill in the art.

"Progroup" refers to a type of protecting group that, when used to mask a functional group within an active quinoline drug to form a promoiety, converts the drug into a prodrug. Progroups are typically attached to the functional group of the drug via bonds that are cleavable under specified conditions of use. Thus, a progroup is that portion of a promoiety that cleaves to release the functional group under the specified conditions of use. As a specific example, an amide promoiety of the formula —NH—C(O)CH$_3$ comprises the progroup —C(O)CH$_3$.

"FcεR1" or "IgE Receptor" refers to the high affinity receptor for the Fc region of IgE found on mast and basophil cells (as well as other cells) that anchors monomeric IgE to the cell surface. The FcεR1 or IgE receptor comprises one alpha, one beta and two gamma chains.

"IgE-Induced Degranulation" or "IgE Receptor-Mediated Degranulation" refers to degranulation that proceeds via the IgE receptor signal transduction cascade initiated by crosslinking of FcεR1-bound IgE. The crosslinking may be induced by an IgE-specific allergen or other multivalent binding agent, such as an anti-IgE antibody. Referring to FIG. 2, the IgE receptor signaling cascade leading to degranulation may be broken into two stages: upstream and downstream. The upstream stage includes all of the processes that occur prior to calcium ion mobilization (illustrated as "Ca$^{2+}$" in FIG. 2). The downstream stage includes calcium ion mobilization and all processes downstream thereof. Compounds that inhibit IgE-induced degranulation may act at any point along the IgE receptor signal transduction cascade. Compounds that selectively inhibit upstream IgE-induced degranulation act to inhibit that portion of the IgE receptor signaling cascade upstream of the point at which calcium ion mobilization is induced. In cell-based assays, compounds that selectively inhibit upstream IgE-induced degranulation inhibit degranulation of mast or basophil cells that are activated or stimulated with an IgE-specific allergen or binding agent (such as an anti-IgE antibody) but do not appreciably inhibit degranulation of mast or basophil cells that are activated or stimulated with degranulating agents that bypass the IgE receptor signaling pathway, such as, for example the calcium ionophores ionomycin and A23187.

"Ionophore-Induced Degranulation" or "Ionophore-Mediated Degranulation" refers to degranulation of a mast or basophil cell that occurs upon exposure to a calcium ionophore such as, for example, ionomycin or A23187.

6.2 The Quinoline Compounds 6.3 The compounds of the invention are generally quinoline compounds according to structural formula (I):

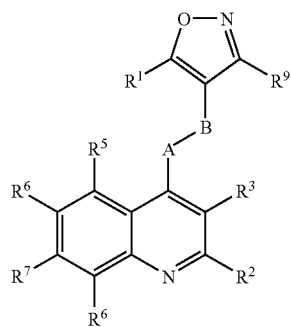

and salts, hydrates, solvates and N-oxides thereof, wherein:

$R^1$ is an alkyl group optionally substituted with one or more of the same or different $R^{10}$ groups;

$R^2$, $R^3$, $R^5$, $R^6$, $R^7$ and $R^8$ are selected from the group consisting of a hydrogen atom, an electronegative group, $-OR^d$, $-SR^d$, (C1-C3) haloalkyloxy, (C1-C3) perhaloalkyloxy, $-N^c$-aryl, $-NR^c$-heteroaryl, halogen, (C1-C3) haloalkyl, (C1-C3) perhaloalkyl, $-CF_3$, $-CH_2CF_3$, $-CF_2CF_3$, (C1-C6) alkyl optionally substituted with one or more of the same or different $R^{10}$ groups, (C5-C 10) aryl optionally substituted with one or more of the same or different $R^{10}$ groups, phenyl optionally substituted with one or more of the same or different $R^{10}$ groups, (5-10 membered heteroaryl optionally substituted with one or more of the same or different $R^{10}$ groups;

$R^9$ is selected from the group consisting of (C1-C3) haloalkyl, (C1-C3) perhaloalkyl, $-CF_3$, $-CH_2CF_3$, $-CF_2CF_3$, (C1-C6) alkyl optionally substituted with one or more of the same or different $R^{10}$ groups, (C5-C10) aryl optionally substituted with one or more of the same or different $R^{10}$ groups, phenyl optionally substituted with one or more of the same or different $R^{10}$ groups;

$R^{10}$ is selected from the group consisting of $R^a$, $R^b$, $R^a$ substituted with one or more of the same or different $R^a$ or $R^b$, $-OR^a$ substituted with one or more of the same or different $R^a$ or $R^b$, $-(CH_2)_m-R^b$, $-(CHR^a)_m-R^b$, $-O-(CH_2)_m-R^b$, $-S-(CH_2)_m-R^b$, $-O-(CHR^a)_m-R^b$;

each $R^a$ is independently selected from the group consisting of hydrogen, (C1-C6) alkyl, (C3-C8) cycloalkyl, cyclohexyl, (C4-C11) cycloalkylalkyl, (C5-C10) aryl, phenyl, (C6-C16) arylalkyl, benzyl;

each $R^b$ is a suitable group independently selected from the group consisting of $-OR^d$, (C1-C3) haloalkyloxy, halogen, $-CF_3$, each $R^c$ is independently a protecting group, $R^a$ or $R^a$ optionally substituted with one or more of the same or different $R^a$ or suitable $R^b$ groups;

each $R^d$ is independently a protecting group, $R^a$ or $R^a$ optionally substituted with one or more of the same or different $R^a$ or suitable $R^b$ groups; and each m is independently an integer from 1 to 3;

A is O, NH or CO

B is CO, NH or O, provided that A and B are not both 0 or either A and B are not O and NH;

with the provisos that:
the compound is not 5-methyl-isoxazole-4-carboxylic acid -(7-chloro)-quinoline or 5-methyl-isoxazole-4-carboxylic acid -(6-fluoro-2-methyl)-quinoline.

In one embodiment, $R^1$ is a methyl group.

In another embodiment, $R^1$ is a methyl group and $R^9$ is a substituted or unsubstituted phenyl group. Suitable substituents on the phenyl group include, for example, halogen atoms such as fluorine, chlorine and combinations thereof.

In still another embodiment, $R^2$ is selected from a hydrogen atom, phenyl groups, methyl, $-CO_2Et$, $-CF_3$, Cl, $-NHCH_3$,

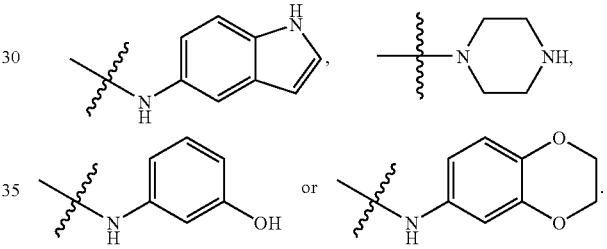

In another embodiment, $R^6$ is a hydrogen atom, F, $-OCF_3$, or Br.

In still yet another embodiment, $R^7$ is a hydrogen atom, Cl or $CF_3$.

In another aspect of the invention, $R^1$ is a methyl group, $R^9$ is a substituted or unsubstituted phenyl group, $R^2$ is a hydrogen atom, a phenyl group, methyl, $-CO_2Et$, $-CF_3$, Cl, $-NHCH_3$,

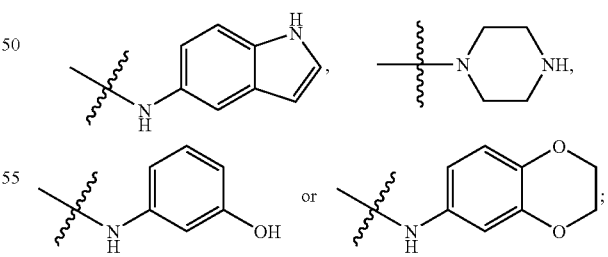

$R^6$ is a hydrogen atom, F, $-OCF_3$, or Br; and $R^7$ is a hydrogen atom, Cl or $-CF_3$.

In another aspect, the compounds of structural formula (I) include any compound selected from TABLE 1 that inhibits mast cell and/or basophil cell degranulation as measured in an in vitro assay, optionally subject to the proviso that the compound is not a compound excluded by the above-described definition. In a specific embodiment, such compounds have an $IC_{50}$ of about 20 µM or less as measured in an in vitro degranulation assay, such as one of the degranulation assays described in the Examples section.

In yet another embodiment, the compounds of structural formulae (I) include any compound selected from TABLE 1 that inhibits the IgE receptor cascade with an $IC_{50}$ of about 20 µM or less as measured in an in vitro assay, such as one of the in vitro assays provided in the Examples section, optionally subject to the proviso that the compound is not a compound excluded by the above-described definition.

Those of skill in the art will appreciate that the quinoline compounds described herein may include functional groups that can be masked with progroups to create prodrugs. Such prodrugs are usually, but need not be, pharmacologically inactive until converted into their active drug form. Indeed, many of the active quinoline compounds described in TABLE 1, infra, include promoieties that are hydrolyzable or otherwise cleavable under conditions of use. For example, ester groups commonly undergo acid-catalyzed hydrolysis to yield the parent carboxylic acid when exposed to the acidic conditions of the stomach. Thus, when administered to a subject orally, quinolines that include ester moieties may be considered prodrugs of their corresponding carboxylic acid, regardless of whether the ester form is pharmacologically active. Referring to TABLE 1, numerous ester-containing quinolines of the invention are active in their ester, "prodrug" form.

In the prodrugs of the invention, any available functional moiety may be masked with a progroup to yield a prodrug. Functional groups within the quinoline compounds that may be masked with progroups for inclusion in a promoiety include, but are not limited to, amines (primary and secondary), hydroxyls, sulfanyls (thiols), carboxyls, etc. Myriad progroups suitable for masking such functional groups to yield promoieties that are cleavable under the desired conditions of use are known in the art. All of these progroups, alone or in combinations, may be included in the prodrugs of the invention.

In one illustrative embodiment, the prodrugs of the invention are compounds according to structural formula (I) in which $R^c$ and $R^d$ may be, in addition to their previously-defined alternatives, a progroup.

Those of skill in the art will appreciate that many of the compounds and prodrugs of the invention, as well as the various compound species specifically described and/or illustrated herein, may exhibit the phenomena of tautomerism, conformational isomerism, geometric isomerism and/or optical isomerism. For example, the compounds and prodrugs of the invention may include one or more chiral centers and/or double bonds and as a consequence may exist as stereoisomers, such as double-bond isomers (i.e., geometric isomers), enantiomers and diasteromers and mixtures thereof, such as racemic mixtures. As another example, the compounds and prodrugs of the invention may exist in several tautomeric forms, including the enol form, the keto form and mixtures thereof. As the various compound names, formulae and compound drawings within the specification and claims can represent only one of the possible tautomeric, conformational isomeric, optical isomeric or geometric isomeric forms, it should be understood that the invention encompasses any tautomeric, conformational isomeric, optical isomeric and/or geometric isomeric forms of the compounds or prodrugs having one or more of the utilities described herein, as well as mixtures of these various different isomeric forms.

Moreover, skilled artisans will appreciate that when lists of alternative substituents include members which, owing to valency requirements or other reasons, cannot be used to substitute a particular group, the list is intended to be read in context to include those members of the list that are suitable for substituting the particular group. For example, skilled artisans will appreciate that while all of the listed alternatives for $R^b$ can be used to substitute an alkyl group, certain of the alternatives, such as =O cannot be used to substitute a phenyl group. It is to be understood that only possible combinations of substituent-group pairs are intended.

The compounds and/or prodrugs of the invention may be identified by either their chemical structure or their chemical name. When the chemical structure and the chemical name conflict, the chemical structure is determinative of the identity of the specific compound.

Depending upon the nature of the various substituents, the quinoline compounds and prodrugs of the invention may be in the form of salts. Such salts include salts suitable for pharmaceutical uses ("pharmaceutically-acceptable salts"), salts suitable for veterinary uses, etc. Such salts may be derived from acids or bases, as is well-known in the art.

In one embodiment, the salt is a pharmaceutically acceptable salt. Generally, pharmaceutically acceptable salts are those salts that retain substantially one or more of the desired pharmacological activities of the parent compound and which are suitable for administration to humans. Pharmaceutically acceptable salts include acid addition salts formed with inorganic acids or organic acids. Inorganic acids suitable for forming pharmaceutically acceptable acid addition salts include, by way of example and not limitation, hydrohalide acids (e.g., hydrochloric acid, hydrobromic acid, etc.), sulfuric acid, nitric acid, phosphoric acid, and the like. Organic acids suitable for forming pharmaceutically acceptable acid addition salts include, by way of example and not limitation, acetic acid, trifluoroacetic acid, propionic acid, hexanoic acid, cyclopentanepropionic acid, glycolic acid, oxalic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, alkylsulfonic acids (e.g., methanesulfonic acid, ethanesulfonic acid, 1,2-ethane-disulfonic acid, 2-hydroxyethanesulfonic acid, etc.), arylsulfonic acids (e.g., benzenesulfonic acid, 4-chlorobenzenesulfonic acid, 2-naphthalenesulfonic acid, 4-toluenesulfonic acid, camphorsulfonic acid, etc.), 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like.

Pharmaceutically acceptable salts also include salts formed when an acidic proton present in the parent compound is either replaced by a metal ion (e.g., an alkali metal ion, an alkaline earth metal ion or an aluminum ion) or coordinates with an organic base (e.g., ethanolamine, diethanolamine, triethanolamine, N-methylglucamine, morpholine, piperidine, dimethylamine, diethylamine, etc.).

The quinoline compounds and of the invention, as well as the salts thereof, may also be in the form of hydrates, solvates and N-oxides, as are well-known in the art.

6.4 Methods of Synthesis

The compounds and prodrugs of the invention may be synthesized via a variety of different synthetic routes using commercially available starting materials and/or starting materials prepared by conventional synthetic methods. Suitable exemplary methods that may be routinely adapted to synthesize the quinoline compounds and prodrugs of the invention are found in WO 94/24095, the disclosure of which is incorporated herein by reference. Specific examples describing the synthesis of numerous compounds and prodrugs of the invention, as well as intermediates therefor, are provided in the Examples section. All of the compounds of structural formulae (I) may be prepared by routine adaptation of these methods.

A variety of exemplary synthetic routes that can be used to synthesize the quinoline compounds of the invention are described in FIG. 4 and Schemes 1 through 6, below. These methods may be routinely adapted to synthesize the quinoline compounds according to formula (I).

6.5 Inhibition of IgE Induced Mast Cell Degranulation

Active quinoline compounds of the invention inhibit the IgE signaling cascade that leads to, among other things, degranulation of mast and/or basophil cells. Both mast and basophil cells play a central role in allergen-induced disorders, including, for example, allergic rhinitis and asthma. Referring to FIG. 1, upon exposure allergens, which may be, among other things, pollen or parasites, allergen-specific IgE antibodies are synthesized by B-cells activated by IL-4 (or IL-13) and other messengers to switch to IgE class specific antibody synthesis. These allergen-specific IgEs bind to the high affinity Fcε receptor (FcεR1 or IgE receptor) present on mast and/or basophil cells. Upon binding of antigen, the FcεR1-bound IgEs are cross-linked and the IgE receptor signal transduction pathway is activated, which leads to degranulation of the cells and consequent release and/or synthesis of a host of chemical mediators, including histamine, proteases (e.g., tryptase and chymase), lipid mediators such as leukotrienes (e.g., LTC4), platelet-activating factor (PAF) and prostaglandins (e.g., PGD2) and a series of cytokines, including TNF-α, IL-4, IL-13, IL-5, IL-6, IL-8, GMCSF, VEGF and TGF-β. The release and/or synthesis of these mediators from mast and/or basophil cells accounts for the early and late stage responses induced by allergens, and is directly linked to downstream events that lead to a sustained inflammatory state.

The molecular events in the IgE receptor signal transduction pathway that lead to release of preformed mediators via degranulation and release and/or synthesis of other chemical mediators are well-known and are illustrated in FIG. 2. Referring to FIG. 2, the IgE receptor (FcεR1) is a heterotetrameric receptor composed of an IgE-binding alpha-subunit, a beta subunit, and two gamma subunits. Cross-linking of IgE-bound IgE receptor by multivalent binding agents (including, for example IgE-specific allergens or anti-IgE antibody) induces the rapid association and activation of the Src-related kinase Lyn. Lyn phosphorylates immunoreceptor tyrosine-based activation motifs (ITAMS) on the intracellular beta and gamma subunits, which leads to the recruitment of additional Lyn to the beta subunit and Syk kinase to the gamma subunits. These receptor-associated kinases, which are activated by intra- and intermolecular phosphorylation, phosphorylate other components of the pathway such as the Btk kinase, LAT, and phospholipase C-gamma. Activated PLC-gamma initiates pathways that lead to protein kinase C activation and $Ca^{2+}$ mobilization, both of which are required for degranulation. FcεR1 cross-linking also activates the three major classes of mitogen activated protein (MAP) kinases, i.e. ERK1/2, JNK1/2, and p38. Activation of these pathways is important in the transcriptional regulation of proinflammatory mediators, such as TNF-α and IL-6, as well as the lipid mediator leukotriene CA (LTC4).

The ability of the quinoline compounds of the invention to inhibit the IgE receptor signaling cascade may be simply determined or confirmed in in vitro assays. Suitable assays are provided in the Examples section. In one typical assay, mast or basophiles are first grown in the presence of IL-4, Stem Cell Factor (SCF), IL-6 and IgE to increase expression of the IgE receptor, exposed to a quinoline test compound of the invention and stimulated with anti-IgE antibodies (or, alternatively, an IgE-specific allergen). Following incubation, the amount of a chemical mediator or other chemical agent released and/or synthesized as a consequence of activating the IgE receptor signaling cascade may be quantified using standard techniques and compared to the amount of the mediator or agent released from control cells (i.e., cells that are stimulated but that are not exposed to test compound). The concentration of test compound that yields a 50% reduction in the quantity of the mediator or agent measured as compared to control cells is the $IC_{50}$ of the test compound. The origin of the mast or basophil cells used in the assay will depend, in part, on the desired use for the compounds and will be apparent to those of skill in the art. For example, if the compounds will be used to treat or prevent a particular disease in humans, a convenient source of mast or basophil cells is a human or other animal which constitutes an accepted or known clinical model for the particular disease. Thus, depending upon the particular application, the mast or basophil cells may be derived from a wide variety of animal sources, ranging from, for example, lower mammals such as mice and rats, to dogs, sheep and other mammals commonly employed in clinical testing, to higher mammals such as monkeys, chimpanzees and apes, to humans. Specific examples of cells suitable for carrying out the in vitro assays include, but are not limited to, rodent or human basophil cells, rat basophil leukemia cell lines, primary mouse mast cells (such as bone marrow-derived mouse mast cells "BMMC") and primary human mast cells isolated from cord blood ("CHMC") or other tissues such as lung. Methods for isolating and culturing these cell types are well-known or are provided in the Examples section (see, e.g., Demo et al., 1999, Cytometry 36(4):340-348 and copending application Ser. No. 10/053,355, filed Nov. 8, 2001, the disclosures of which are incorporated herein by reference).

As will be recognized by skilled artisans, the mediator or agent quantified is not critical. The only requirement is that it be a mediator or agent released and/or synthesized as a consequence of initiating or activating the IgE receptor signaling cascade. Referring to FIG. 1, activation of this signaling cascade leads to numerous downstream events. For example, activation of the IgE receptor signal cascade leads to the immediate release (i.e., within 1-3 min. following receptor activation) of a variety of preformed chemical mediators and agents via degranulation. Thus, in one embodiment, the mediator or agent quantified may be specific to granules (i.e., present in granules but not in the cell cytoplasm generally). Examples of granule-specific mediators or agents that can be quantified to determine and/or confirm the activity of a quinoline compound of the invention include, but are not limited to, granule-specific enzymes such as hexosaminidase and tryptase and granule-specific components such as histamine and serotonin. Assays for quantifying such factors are well-known, and in many instances are commercially available. For example, tryptase and/or hexosaminidase release may be quantified by incubating the cells with cleavable substrates that fluoresce upon cleavage and quantifying the amount of fluorescence produced using conventional techniques. Such cleavable fluorogenic substrates are commercially available. For example, the fluorogenic substrates Z-Gly-Pro-Arg-AMC (Z=benzyloxycarbonyl; AMC=7-amino-4-methylcoumarin; BIOMOL Research Laboratories, Inc., Plymouth Meeting, Pa. 19462, Catalog No. P-142) and Z-Ala-Lys-Arg-AMC (Enzyme Systems Products, a division of ICN Biomedicals, Inc., Livermore, Calif. 94550, Catalog No. AMC-246) can be used to quantify the amount of tryptase released. The fluorogenic substrate 4-methylumbelliferyl-N-acetyl-β-

D-glucosaminide (Sigma, St. Louis, Mo., Catalog #69585) can be used to quantify the amount of hexosaminidase released. Histamine release may be quantified using a commercially available enzyme-linked immunosorbent assay (ELISA) such as Immunotech histamine ELISA assay #IM2015 (Beckman-Coulter, Inc.). Specific methods of quantifying the release of tryptase, hexosaminidase and histamine are provided in the Examples section. Any of these assays may be used to determine or confirm the activity of the quinoline compounds of the invention.

Referring again to FIG. 1, degranulation is only one of several responses initiated by the IgE receptor signaling cascade. In addition, activation of this signaling pathway leads to the de novo synthesis and release of cytokines and chemokines such as IL-4, IL-5, IL-6, TNF-α, IL-13 and MIP1-α), and release of lipid mediators such as leukotrienes (e.g., LTC4), platelet activating factor (PAF) and prostaglandins. Accordingly, the quinoline compounds of the invention may also be assessed for activity by quantifying the amount of one or more of these mediators released and/or synthesized by activated cells.

Unlike the granule-specific components discussed above, these "late stage" mediators are not released immediately following activation of the IgE receptor signaling cascade. Accordingly, when quantifying these late stage mediators, care should be taken to insure that the activated cell culture is incubated for a time sufficient to result in the synthesis (if necessary) and release of the mediator being quantified. Generally, PAF and lipid mediators such as leukotriene C4 are released 3-30 min. following IgE receptor activation. The cytokines and other late stage mediators are released approx. 4-8 hrs. following IgE receptor activation. Incubation times suitable for a specific mediator will be apparent to those of skill in the art. Specific guidance and assays are provided in the Examples section.

The amount of a particular late stage mediator released may be quantified using any standard technique. In one embodiment, the amount(s) may be quantified using ELISA assays. ELISA assay kits suitable for quantifying the amount of TNFα, IL-4, IL-5, IL-6 and/or IL-13 released are available from, for example, Biosource International, Inc., Camarillo, Calif. 93012 (see, e.g., Catalog Nos. KHC3011, KHC0042, KHC0052, KHC0061 and KHC0132). ELISA assay kits suitable for quantifying the amount of leukotriene C4 (LTC4) released from cells are available from Cayman Chemical Co., Ann Arbor, Mich. 48108 (see, e.g., Catalog No. 520211).

Typically, active quinoline compounds of the invention will exhibit $IC_{50}$s with respect to IgE-induced or IgE receptor-mediated degranulation and/or mediator release or synthesis of about 20 μM or lower, as measured in an in vitro assay, such as one of the in vitro assays described above or in the Examples section. Of course, skilled artisans will appreciate that compounds which exhibit lower $IC_{50}$s, for example on the order of 10 μM, 1 μM, 100 nM, 10 nM, 1 nM, or even lower, are particularly useful. Skilled artisans will appreciate that the various mediators discussed above may induce different adverse effects or exhibit different potencies with respect to the same adverse effect. For example, the lipid mediator LCT4 is a potent vasoconstrictor—it is approximately 1000-fold more potent at inducing vasoconstriction than histamine. As another example, in addition to mediating atopic or Type I hypersensitivity reactions, cytokines can also cause tissue remodeling and cell proliferation. Thus, although compounds that inhibit release and/or synthesis of any one of the previously discussed chemical mediators are useful, skilled artisans will appreciate that compounds which inhibit the release and/or synthesis of a plurality, or even all, of the previously described mediators find particular use, as such compounds are useful for ameliorating or avoiding altogether a plurality, or even all, of the adverse effects induced by the particular mediators. For example, compounds which inhibit the release of all three types of mediators—granule-specific, lipid and cytokine—are useful for treating or preventing immediate Type I hypersensitivity reactions as well as the chronic symptoms associated therewith.

Compounds of the invention capable of inhibiting the release of more than one type of mediator (e.g., granule-specific or late stage) may be identified by determining the $IC_{50}$ with respect to a mediator representative of each class using the various in vitro assays described above (or other equivalent in vitro assays). Compounds of the invention which are capable of inhibiting the release of more than one mediator type will typically exhibit an $IC_{50}$ for each mediator type tested of less than about 20 μM. For example, a compound which exhibits an $IC_{50}$ of 1 μM with respect to histamine release ($IC_{50}^{histamine}$) and an $IC_{50}$ of 1 nM with respect to leukotriene LTC4 synthesis and/or release ($IC_{50}^{LTC4}$) inhibits both immediate (granule-specific) and late stage mediator release. As another specific example, a compound that exhibits an $IC_{50}^{tryptase}$ of 10 μM, an $IC_{50}^{LTC4}$ of 1 μM and an $IC_{50}^{IL-4}$ of 1 μM inhibits immediate (granule-specific), lipid and cytokine mediator release. Although the above specific examples utilize the $IC_{50}$s of one representative mediator of each class, skilled artisans will appreciate that the $IC_{50}$s of a plurality, or even all, mediators comprising one or more of the classes may be obtained. The quantity(ies) and identity(ies) of mediators for which $IC_{50}$ data should be ascertained for a particular compound and application will be apparent to those of skill in the art.

One particularly useful class of compounds includes those quinoline compounds that inhibit the release of immediate granule-specific mediators and late stage mediators with approximately equivalent $IC_{50}$s. By approximately equivalent is meant that the $IC_{50}$s for each mediator type are within about a 10-fold range of one another. Another particularly useful class of compounds includes those quinoline compounds that inhibit the release of immediate granule-specific mediators, lipid mediators and cytokine mediators with approximately equivalent $IC_{50}$s. In a specific embodiment, such compounds inhibit the release of the following mediators with approximately equivalent $IC_{50}$s: histamine, tryptase, hexosaminidase, IL-4, IL-5, IL-6, IL-13, TNFα and LTC4. Such compounds are particularly useful for, among other things, ameliorating or avoiding altogether both the early and late stage responses associated with atopic or immediate Type I hypersensitivity reactions.

Ideally, the ability to inhibit the release of all desired types of mediators will reside in a single compound. However, mixtures of compounds can also be identified that achieve the same result. For example, a first compound which inhibits the release of granule specific mediators may be used in combination with a second compound which inhibits the release and/or synthesis of cytokine mediators.

In addition to the IgE-induced (or IgE receptor-mediated) degranulation pathway discussed above, degranulation of mast and/or basophil cells can be induced by other agents. For example, ionomycin, a calcium ionophore that bypasses the early IgE receptor signal transduction machinery of the cell, directly induces a calcium flux that triggers degranulation. Referring again to FIG. 2, activated PLCγ initiates pathways that lead to, among other things, calcium ion mobilization and subsequent degranulation. As illustrated, this $Ca^{2+}$ mobilization is triggered late in the IgE receptor signal transduction pathway. As mentioned above, and as illustrated in FIG. 3, ionomycin directly induces $Ca^{2+}$ mobilization and a $Ca^{2+}$ flux that leads to degranulation. Other ionophores that induce degranulation in this manner include A23187. The ability of granulation-inducing ionophores such as ionomycin to bypass the early stages of the IgE receptor signaling cascade may be used as a counter screen to identify active compounds of the invention that specifically exert their degranulation-inhibitory activity by blocking or inhibiting the early IgE receptor signaling cascade that is initiated when the IgE receptor is cross-linked by antigen. Compounds which specifically inhibit such early IgE receptor mediated degranulation inhibit not only degranulation and subsequent rapid release of histamine, tryptase and other granule contents, but also inhibit the pro-inflammatory activation pathways causing the release of TNFα, IL-4, IL-13 and the lipid mediators such as LTC4. Thus, compounds which specifically inhibit such early IgE receptor-mediated degranulation block or inhibit not only acute atopic or Type1 hypersensitivity reactions, but also late responses involving multiple inflammatory mediators.

Compounds of the invention that specifically inhibit early IgE receptor mediated mast and/or basophil degranulation are those compounds that inhibit IgE-induced degranulation (for example, have an $IC_{50}$ of less than about 20 μM with respect to the release of a granule-specific mediator or component as measured in an in vitro assay with cells stimulated with an IgE binding agent) but that do not appreciably inhibit ionophore-induced degranulation. In one embodiment, compounds are considered to not appreciably inhibit ionophore-induced degranulation if they exhibit an $IC_{50}$ of ionophore-induced degranulation of greater than about 20 μM, as measured in an in vitro assay. Of course, active compounds that exhibit even higher $IC_{50}$s of ionophore-induced degranulation, or that do not inhibit ionophore-induced degranulation at all, are particularly useful. In another embodiment, compounds are considered to not appreciably inhibit ionophore-induced degranulation if they exhibit a greater than 10-fold difference in their $IC_{50}$s of IgE-receptor-mediated degranulation and ionophore-induced degranulation, as measured in an in vitro assay. Assays suitable for determining the $IC_{50}$ of ionophore-induced degranulation include any of the previously-described degranulation assays, with the modification that the cells are stimulated or activated with a degranulation-inducing calcium ionophore such as ionomycin or A23187 (A.G. Scientific, San Diego, Calif.) instead of anti-IgE antibodies or an IgE-specific allergen. Specific assays for assessing the ability of a particular quinoline compound of the invention to inhibit ionophore-induced degranulation are provided in the Examples section.

As will be recognized by skilled artisans, compounds which exhibit a high degree of selectivity of IgE-induced degranulation find particular use, as such compounds selectively target the IgE receptor cascade and do not interfere with other degranulation mechanisms. Compounds which exhibit a high degree of selectivity are generally 10-fold or more selective for IgE-induced degranulation over ionophore-induced degranulation, such as ionomycin-induced degranulation.

6.6 Uses and Compositions

As previously discussed, the active compounds of the invention inhibit the IgE receptor signaling cascade leading to the release and/or synthesis of chemical mediators from mast and/or basophil cells, either via degranulation or other processes. As also discussed, many of the active compounds exert their inhibitory activity by acting early in the IgE receptor signal transduction pathway. As a consequence of these activities, the active compounds of the invention may be used in a variety of in vitro, in vivo and ex vivo contexts to regulate or inhibit the release of chemical mediators from mast and/or basophil cells. For example, in one embodiment, the compounds may be used as controls or standards in in vitro or in vivo screening assays to identify other compounds capable of inhibiting mast and/or basophil degranulation. In another embodiment, the active compounds may be used to regulate or inhibit the IgE receptor signaling cascade and/or IgE-induced mast and/or basophil degranulation as a therapeutic approach towards the treatment or prevention of diseases characterized by, caused by and/or associated with the release or synthesis of chemical mediators or IgE-induced mast and/or basophil degranulation. Such treatments may be administered to animals in veterinary contexts or to humans. Diseases that are characterized by, caused by or associated with such mediator release, synthesis or degranulation, and that can therefore be treated or prevented with the active compounds include, by way of example and not limitation, atopy or anaphylactic hypersensitivity or allergic reactions, allergies (e.g., allergic conjunctivitis, allergic rhinitis, atopic asthma, atopic dermatitis and food allergies), low grade scarring (e.g., of scleroderma, increased fibrosis, keloids, post-surgical scars, pulmonary fibrosis, vascular spasms, migraine, reperfusion injury and post myocardial infarction), diseases associated with tissue destruction (e.g., of COPD, cardiobronchitis and post myocardial infarction), diseases associated with tissue inflammation (e.g., irritable bowel, spastic colon and inflammatory colon disease), inflammation, certain autoimmune diseases (e.g., lupus, rheumatoid arthritis, multiple sclerosis, etc.) and scarring.

When used to treat or prevent such diseases, the active compounds may be administered singly, as mixtures of one or more active compounds or in mixture or combination with other agents useful for treating such diseases and/or the symptoms associated with such diseases. The active compounds may also be administered in mixture or in combination with agents useful to treat other disorders or maladies, such as steroids, membrane stablizers, 5LO inhibitors, leukotriene synthesis and receptor inhibitors, inhibitors of IgE isotype switching or IgE synthesis, β-agonists, tryptase inhibitors and antihistamines, to name a few. The active compounds may be administered per se in the form of prodrugs or as pharmaceutical compositions, comprising an active compound or prodrug.

Pharmaceutical compositions comprising the active compounds of the invention (or prodrugs thereof) may be manufactured by means of conventional mixing, dissolving, granulating, dragee-making levigating, emulsifying, encapsulating, entrapping or lyophilization processes. The compositions may be formulated in conventional manner using one or more physiologically acceptable carriers, diluents, excipients or auxiliaries which facilitate processing of the active compounds into preparations which can be used pharmaceutically.

The active compound or prodrug may be formulated in the pharmaceutical compositions per se, or in the form of a hydrate, solvate, N-oxide or pharmaceutically acceptable salt, as previously described. Typically, such salts are more soluble in aqueous solutions than the corresponding free acids and bases, but salts having lower solubility than the corresponding free acids and bases may also be formed.

Pharmaceutical compositions of the invention may take a form suitable for virtually any mode of administration, including, for example, topical, ocular, oral, baccal, systemic, nasal, injection, transdermal, rectal, vaginal, etc., or a form suitable for administration by inhalation or insufflation.

For topical administration, the active compound(s) or prodrug(s) may be formulated as solutions, gels, ointments, creams, suspensions, etc. as are well-known in the art.

Systemic formulations include those designed for administration by injection, e.g., subcutaneous, intravenous, intramuscular, intrathecal or intraperitoneal injection, as well as those designed for transdermal, transmucosal oral or pulmonary administration.

Useful injectable preparations include sterile suspensions, solutions or emulsions of the active compound(s) in aqueous or oily vehicles. The compositions may also contain formulating agents, such as suspending, stabilizing and/or dispersing agent. The formulations for injection may be presented in unit dosage form, e.g., in ampules or in multidose containers, and may contain added preservatives.

Alternatively, the injectable formulation may be provided in powder form for reconstitution with a suitable vehicle, including but not limited to sterile pyrogen free water, buffer, dextrose solution, etc., before use. To this end, the active compound(s) may dried by any art-known technique, such as lyophilization, and reconstituted prior to use.

For transmucosal administration, penetrants appropriate to the barrier to be permeated are used in the formulation. Such penetrants are known in the art.

For oral administration, the pharmaceutical compositions may take the form of, for example, lozenges, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets may be coated by methods well known in the art with, for example, sugars or enteric coatings.

Liquid preparations for oral administration may take the form of, for example, elixirs, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, preservatives, flavoring, coloring and sweetening agents as appropriate.

Preparations for oral administration may be suitably formulated to give controlled release of the active compound or prodrug, as is well known.

For buccal administration, the compositions may take the form of tablets or lozenges formulated in conventional manner.

For rectal and vaginal routes of administration, the active compound(s) may be formulated as solutions (for retention enemas) suppositories or ointments containing conventional suppository bases such as cocoa butter or other glycerides.

For nasal administration or administration by inhalation or insufflation, the active compound(s) or prodrug(s) can be conveniently delivered in the form of an aerosol spray from pressurized packs or a nebulizer with the use of a suitable propellant, e.g., dichlorodifluoromethane, trichlorofluoromethane, dichlorotetrafluoroethane, fluorocarbons, carbon dioxide or other suitable gas. In the case of a pressurized aerosol, the dosage unit may be determined by providing a valve to deliver a metered amount. Capsules and cartridges for use in an inhaler or insufflator (for example capsules and cartridges comprised of gelatin) may be formulated containing a powder mix of the compound and a suitable powder base such as lactose or starch.

A specific example of an aqueous suspension formulation suitable for nasal administration using commercially-available nasal spray devices includes the following ingredients: active compound or prodrug (0.5-20 mg/ml); benzalkonium chloride (0.1-0.2 mg/mL); polysorbate 80 (TWEEN® 80; 0.5-5 mg/ml); carboxymethylcellulose sodium or microcrystalline cellulose (1-15 mg/ml); phenylethanol (1-4 mg/ml); and dextrose (20-50 mg/ml). The pH of the final suspension can be adjusted to range from about pH5 to pH7, with a pH of about pH 5.5 being typical.

For ocular administration, the active compound(s) or prodrug(s) may be formulated as a solution, emulsion, suspension, etc. suitable for administration to the eye. A variety of vehicles suitable for administering compounds to the eye are known in the art. Specific non-limiting examples are described in U.S. Pat. Nos. 6,261,547; 6,197,934; 6,056,950; 5,800,807; 5,776,445; 5,698,219; 5,521,222; 5,403,841; 5,077,033; 4,882,150; and 4,738,851.

For prolonged delivery, the active compound(s) or prodrug(s) can be formulated as a depot preparation for administration by implantation or intramuscular injection. The active ingredient may be formulated with suitable polymeric or hydrophobic materials (e.g., as an emulsion in an acceptable oil) or ion exchange resins, or as sparingly soluble derivatives, e.g., as a sparingly soluble salt. Alternatively, transdermal delivery systems manufactured as an adhesive disc or patch which slowly releases the active compound(s) for percutaneous absorption may be used. To this end, permeation enhancers may be used to facilitate transdermal penetration of the active compound(s). Suitable transdermal patches are described in for example, U.S. Pat. Nos. 5,407,713; 5,352,456; 5,332,213; 5,336,168; 5,290,561; 5,254,346; 5,164,189; 5,163,899; 5,088,977; 5,087,240; 5,008,110; and 4,921,475.

Alternatively, other pharmaceutical delivery systems may be employed. Liposomes and emulsions are well-known examples of delivery vehicles that may be used to deliver active compound(s) or prodrug(s). Certain organic solvents such as dimethylsulfoxide (DMSO) may also be employed, although usually at the cost of greater toxicity.

The pharmaceutical compositions may, if desired, be presented in a pack or dispenser device which may contain one or more unit dosage forms containing the active compound(s). The pack may, for example, comprise metal or plastic foil, such as a blister pack. The pack or dispenser device may be accompanied by instructions for administration.

6.7 Effective Dosages

The active compound(s) or prodrug(s) of the invention, or compositions thereof, will generally be used in an amount effective to achieve the intended result, for example in an amount effective to treat or prevent the particular disease being treated. The compound(s) may be administered therapeutically to achieve therapeutic benefit or prophylactically to achieve prophylactic benefit. By therapeutic benefit is meant eradication or amelioration of the underlying disorder being treated and/or eradication or amelioration of one or more of the symptoms associated with the underlying disorder such that the patient reports an improvement in feeling or condition, notwithstanding that the patient may still be afflicted with the underlying disorder. For example, administration of a compound to a patient suffering from an allergy provides therapeutic benefit not only when the underlying allergic response is eradicated or ameliorated, but also when the patient reports a decrease in the severity or duration of the symptoms associated with the allergy following exposure to the allergen. As another example, therapeutic benefit in the context of asthma includes an improvement in respiration following the onset of an asthmatic attack, or a reduction in the frequency or severity of asthmatic episodes. Therapeutic benefit also includes halting or slowing the progression of the disease, regardless of whether improvement is realized.

For prophylactic administration, the compound may be administered to a patient at risk of developing one of the previously described diseases. For example, if it is unknown whether a patient is allergic to a particular drug, the compound may be administered prior to administration of the drug to avoid or ameliorate an allergic response to the drug. Alternatively, prophylactic administration may be applied to avoid the onset of symptoms in a patient diagnosed with the underlying disorder. For example, a compound may be administered to an allergy sufferer prior to expected exposure to the allergen. Compounds may also be administered prophylactically to healthy individuals who are repeatedly exposed to agents known to one of the above-described maladies to prevent the onset of the disorder. For example, a compound may be administered to a healthy individual who is repeatedly exposed to an allergen known to induce allergies, such as latex, in an effort to prevent the individual from developing an allergy. Alternatively, a compound may be administered to a patient suffering from asthma prior to partaking in activities which trigger asthma attacks to lessen the severity of, or avoid altogether, an asthmatic episode.

The amount of compound administered will depend upon a variety of factors, including, for example, the particular indication being treated, the mode of administration, whether the desired benefit is prophylactic or therapeutic, the severity of the indication being treated and the age and weight of the patient, the bioavailability of the particular active compound, etc. Determination of an effective dosage is well within the capabilities of those skilled in the art.

Effective dosages may be estimated initially from in vitro assays. For example, an initial dosage for use in animals may be formulated to achieve a circulating blood or serum concentration of active compound that is at or above an $IC_{50}$ of the particular compound as measured in as in vitro assay, such as the in vitro CHMC or BMMC and other in vitro assays described in the Examples section. Calculating dosages to achieve such circulating blood or serum concentrations taking into account the bioavailability of the particular compound is well within the capabilities of skilled artisans. For guidance, the reader is referred to Fingl & Woodbury, "General Principles," In: *Goodman and Gilman's The Pharmaceutical Basis of Therapeutics*, Chapter 1, pp. 1-46, latest edition, Pagamonon Press, and the references cited therein.

Initial dosages can also be estimated from in vivo data, such as animal models. Animal models useful for testing the efficacy of compounds to treat or prevent the various diseases described above are well-known in the art. Suitable animal models of hypersensitivity or allergic reactions are described in Foster, 1995, Allergy 50(21 Suppl):6-9, discussion 34-38 and Tumas et al., 2001, J. Allergy Clin. Immunol. 107(6): 1025-1033. Suitable animal models of allergic rhinitis are described in Szelenyi et al., 2000, Arzneimittelforschung 50(11):1037-42; Kawaguchi et al., 1994, Clin. Exp. Allergy 24(3):238-244 and Sugimoto et al., 2000, Immunopharmacology 48(1): 1-7. Suitable animal models of allergic conjunctivitis are described in Carreras et al., 1993, Br. J. Ophthalmol. 77(8):509-514; Saiga et al., 1992, Ophthalmic Res. 24(1):45-50; and Kunert et al., 2001, Invest. Ophthalmol. Vis. Sci. 42(11):2483-2489. Suitable animal models of systemic mastocytosis are described in O'Keefe et al., 1987, J. Vet. Intern. Med. 1(2):75-80 and Bean-Knudsen et al., 1989, Vet. Pathol. 26(1):90-92. Suitable animal models of hyper IgE syndrome are described in Claman et al., 1990, Clin. Immunol. Immunopathol. 56(1):46-53. Suitable animal models of B-cell lymphoma are described in Hough et al., 1998, Proc. Natl. Acad. Sci. USA 95:13853-13858 and Hakim et al., 1996, J. Immunol. 157(12):5503-5511. Suitable animal models of atopic disorders such as atopic dermatitis, atopic eczema and atopic asthma are described in Chan et al., 2001, J. Invest. Dermatol. 117(4):977-983 and Suto et al., 1999, Int. Arch. Allergy Immunol. 120(Suppl 1):70-75. Ordinarily skilled artisans can routinely adapt such information to determine dosages suitable for human administration. Additional suitable animal models are described in the Examples section.

Dosage amounts will typically be in the range of from about 0.0001 or 0.001 or 0.01 mg/kg/day to about 100 mg/kg/day, but may be higher or lower, depending upon, among other factors, the activity of the compound, its bioavailability, the mode of administration and various factors discussed above. Dosage amount and interval may be adjusted individually to provide plasma levels of the compound(s) which are sufficient to maintain therapeutic or prophylactic effect. In cases of local administration or selective uptake, such as local topical administration, the effective local concentration of active compound(s) may not be related to plasma concentration. Skilled artisans will be able to optimize effective local dosages without undue experimentation.

The compound(s) may be administered once per day, a few or several times per day, or even multiple times per day, depending upon, among other things, the indication being treated and the judgment of the prescribing physician.

Preferably, the compound(s) will provide therapeutic or prophylactic benefit without causing substantial toxicity. Toxicity of the compound(s) may be determined using standard pharmaceutical procedures. The dose ratio between toxic and therapeutic (or prophylactic) effect is the therapeutic index. Compounds(s) that exhibit high therapeutic indices are preferred.

The invention having been described, the following examples are offered by way of illustration and not limitation.

7. EXAMPLES

7.1 Synthesis of Starting Materials and Intermediates

Schemes 1 through 3 provide methods to synthesize intermediates useful for the preparation of the quinoline compounds of the present invention. Schemes 1 through 3 are representative examples of how such compounds can be prepared. One skilled in the art can prepare compounds having varous substitutents appended to the quinoline portion of the molecule as well as the isoxazole portion of the molecule, wherein the substitutents are as defined above.

7.1.1 Synthesis of Isoxazole Acyl Chlorides

Isoxazole acyl chlorides were prepared from isoxazole carboxylic acids and $PCl_5$ as shown in Scheme 1.

7.1.2 Synthesis of Quinoline Acyl Chlorides

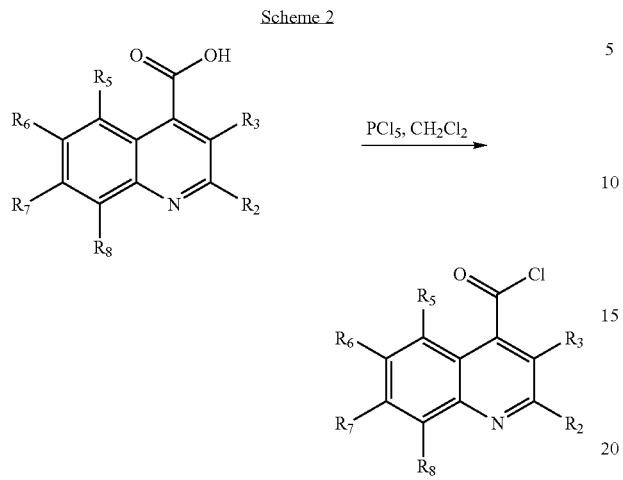

Quinoline acyl chlorides were prepared from quinoline carboxylic acids and $PCl_5$ as shown in Scheme 2.

7.1.3 Synthesis of Aminoquinolines

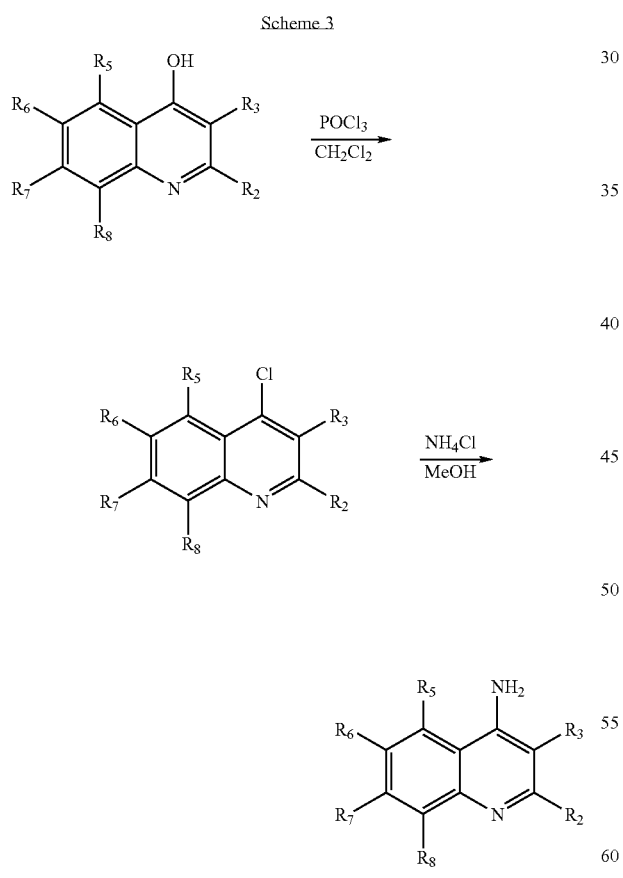

4-Hydroxyquinolines can be converted into 4-aminoquinolines using a two step procedure. Treatment of 4-hydroxyquinolines with $POCl_3$ gave 4-chloroquinolines, subsequent treatment with ammonium chloride produced desired 4-aminoquinolines as shown in Scheme 3.

7.2 Synthesis of Ester Linked Compounds of the Invention

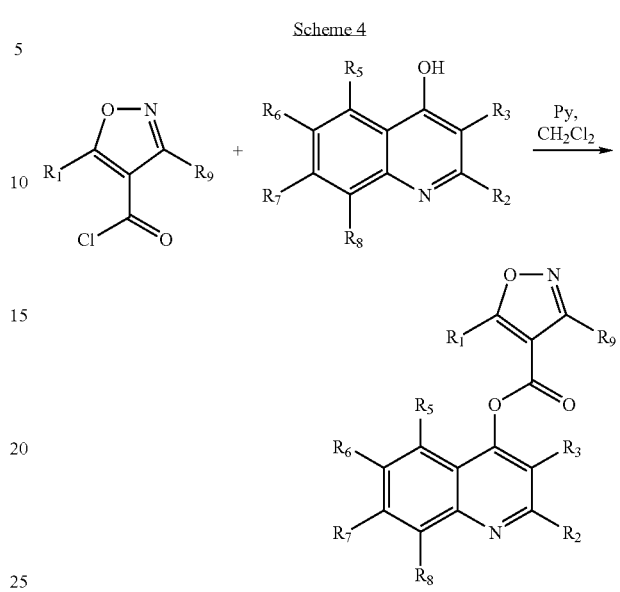

Isoxazole acyl chlorides and 4-hydroxyquinolines were coupled under standard conditions to give ester-linked compounds as shown in Scheme 4.

7.3 Synthesis of Amide Linked Compounds of the Invention

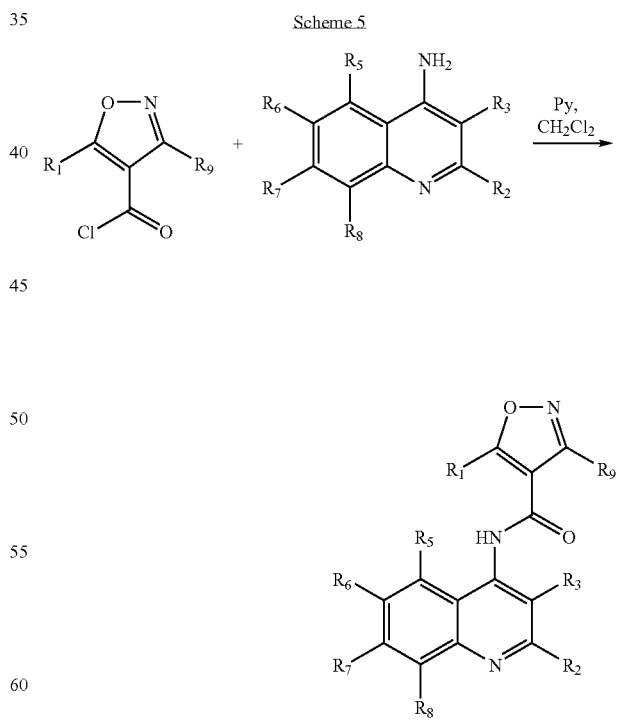

Under conditions similar to those used to prepare ester linked compounds of the invention, isoxazole acyl chlorides and 4-aminoquinolines were coupled to produce amide-linked compounds as shown in Scheme 5.

7.4 Synthesis of Reverse-Amide Linked Compounds of the Invention

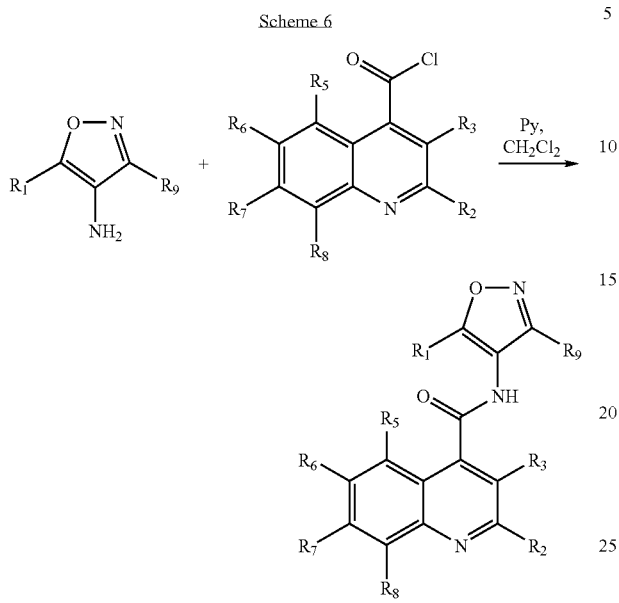

Under conditions similar to those used to prepare amide linked or ester linked compounds of the invention, isoxazole amines and 4-acylquinolines were coupled to produce rever-amide lined compounds as shown in Scheme 6.

7.5 SNAr Reactions with Quinoline Compounds

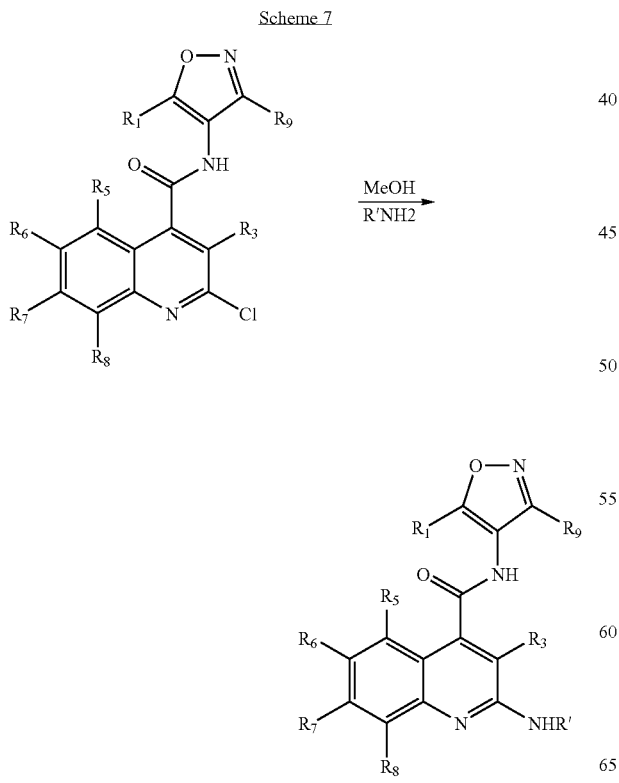

2-Chloroquinoline compounds can be converted to 2-amino substituted analogs using amines, anilines and indoles as shown in Scheme 7.

7.6 Preparative Examples

7.6.1 Example 9

5-Methyl-3-phenyl-4-isoxazolecarboxylic acid, 2-methyl-4-quinolinyl Ester (Compound 9)

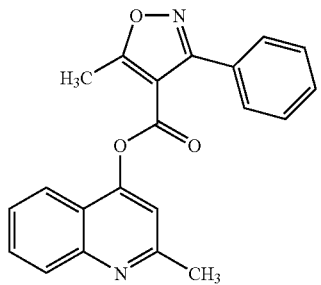

A solution of 5-methyl-3-phenylisoxazole-4-carboxylic acid (1 g) and $PCl_5$ (1 g) in dichloromethane (20 mL) was refluxed for one hour. Then dichloromethane and $POCl_3$ were removed under reduced pressure to give 5-methyl-3-phenyl-isoxazole-4-carbonyl chloride.

5-Methyl-3-phenylisoxazole-4-carbonyl chloride (100 mg) and 4-hydroxy-2-methylquinoline (250 mg) were dissolved in dichlorormethane (10 mL) and pyridine (0.2 mL). The reaction solution was heated at 70° C. overnight and then diluted with ethyl acetate (60 mL). The organic solution was washed with water (60 mL), dried, evaporated and purified by flash column chromatography (EtOAc/hexanes=1/2) to give 5-methyl-3-phenyl-4-isoxazolecarboxylic acid, 2-methyl-4-quinolinyl ester (100 mg). $^1$H NMR (CDCl$_3$): δ 2.74 (s, 3H), 2.91 (s, 3H), 7.29 (s, 1H), 7.33-7.46 (m, 5H), 7.64-7.71 (m, 3H), 8.01 (td, J=0.9 and 8.4 Hz, 1H); LCMS: ret. time: 23.10 min.; purity: 100%; MS (m/e): 345.02 (MH$^+$).

7.6.2 Example 35

5-Methyl-3-phenyl-N-(7-trifluoromethyl-4-quinoli-nyl)-4-isoxazolecarboxamide (Compound 35)

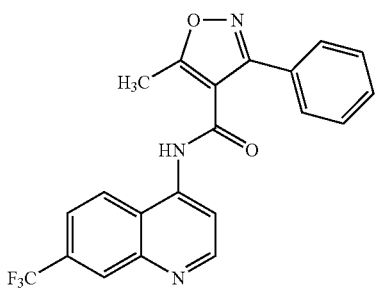

A solution of 4-hydroxy-7-trifluoromethylquinoline (1 g) in dichloromethane (10 mL) and $POCl_3$ (1 mL) was refluxed for half an hour. Then the reaction mixture was quenched with water (80 mL) and sodium bicarbonate to pH 7. The aqueous solution was extracted with dichloromethane (2×60 mL). The organic layers were combined, dried, evaporated to give 4-chloro-7-trifluoromethylquinoline. LCMS: ret. time: 31.51 min.; purity: 100%; MS (m/e): 232 (MH+).

A solution of 4-chloro-7-trifluoromethylquinoline (1 g) and ammonium chloride (1 g) in methanol (10 mL) was heated at 70° C. overnight. Then the solid was filtered off and washed with methanol. The filtrated was evaporated to give 4-amino-7-trifluoromethylquinoline. LCMS: ret. time: 14.81 min.; purity: 82.25%; MS (m/e): 228.11 (M+16).

5-Methyl-3-phenylisoxazole-4-carbonyl chloride (100 mg) and 4-amino-7-trifluoromethylquinoline (250 mg) were dissolved in dichlorormethane (5 mL) and pyridine (0.3 mL). The reaction solution was heated at 70° C. overnight and then diluted with ethyl acetate (60 mL). The organic solution was washed with water (60 mL), dried, evaporated and purified by flash column chromatography (EtOAc/hexanes=1/6) to give 5-methyl-3-phenyl-N-(7-trifluoromethyl-4-quinolinyl)-4-isoxazolecarboxamide (100 mg) as a white solid. $^1$H NMR (CDCl$_3$): δ 2.91 (s, 3H), 7.33-7.69 (m, 9H), 8.39 (s, 1H, NH), 8.99 (d, J=5.1 Hz, 1H); $^{19}$F NMR (282 MHz, CDCl$_3$): δ-63.26; LCMS: ret. time: 34.04 min.; purity: 98.90%; MS (m/e): 398.77 (MH+).

7.6.3 Example 47

6-Fluoro-2-methyl-N-(5-methyl-3-phenylisoxazol-4-yl)-4-quinolinecarboxamide (Compound 47)

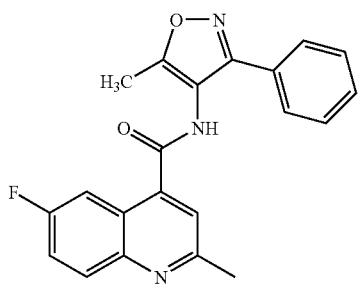

A solution of 6-fluoro-2-methylquinoline-4-carboxylic acid (500 mg) and PCl$_5$ (500 mg) in dichloromethane (10 mL) was refluxed for half an hour. Then dichloromethane and POCl$_3$ were removed under reduced pressure to give 6-fluoro-2-methylquinoline-4-carbonyl chloride.

6-Fluoro-2-methylquinoline-4-carbonyl chloride (100 mg) and 4-amino-5-methyl-3-phenylisoxazole (200 mg) were dissolved in dichlorormethane (10 mL) and pyridine (0.3 mL). The reaction solution was heated at 70° C. overnight and then diluted with ethyl acetate (60 mL). The organic solution was washed with water (60 mL), dried, evaporated and purified by flash column chromatography (EtOAc/hexanes=1/1) to give 6-fluoro-2-methyl-N-(5-methyl-3-phenylisoxazol-4-yl)-4-quinolinecarboxamide (100 mg) as a white solid. $^1$H NMR (CDCl$_3$): δ 2.58 (s, 3H), 2.76 (s, 3H), 7.14 (s, 1H), 7.44 (s, 1H), 7.49 (m, 4H), 7.67 (m, 2H), 7.82 (dd, J=2.7 and 9.9 Hz, 1H), 8.07 (dd, J=5.7 and 9.3 Hz, 1H); $^{19}$F NMR (282 MHz, CDCl$_3$): δ-111.63; LCMS: ret. time: 21.32 min.; purity: 99.44%; MS (m/e): 362.06 (MH+).

7.6.4 Example 71

6-Bromo-2-(3-hydroxyphenyl)amino-N-(5-methyl-3-phenylisoxazol-4-yl)-4-quinolinecarboxamide (Compound 71)

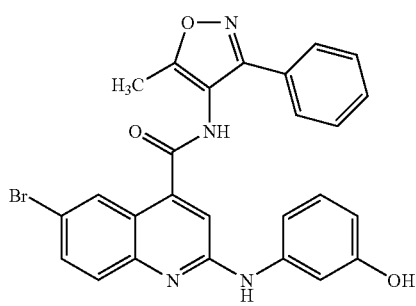

6-Bromo-2-chloroquinoline-4-carbonyl chloride (500 mg) and 4-amino-5-methyl-3-phenylisoxazole (400 mg) were dissolved in dichlorormethane (15 mL) and pyridine (1 mL). The reaction solution was heated at 70° C. overnight. The white precipitation was collected by filtration, washed with ethyl acetate and dried to give 6-bromo-2-chloro-N-(5-methyl-3-phenylisoxazol-4-yl)-4-quinolinecarboxamide (520 mg) as a white solid. $^1$H NMR (DMSO-d$_6$): δ 2.52 (s, 3H), 7.52 (m, 3H), 7.72 (m, 2H), 8.02 (m, 4H), 10.58 (s, 1H); LCMS: ret. time: 32.23 min.; purity: 100%; MS (m/e): 441.82 (M+).

The solution of 6-bromo-2-chloro-N-(5-methyl-3-phenyl-isoxazol-4-yl)-4-quinolinecarboxamide (50 mg) and 3-aminophenol (50 mg) in ethanol (2 mL) and triethylamine (0.1 mL) was microwaved at 170° C. for one hour. The reaction mixture was then diluted with ethyl acetate (60 mL). The organic solution was washed with water (60 mL), 1N HCl aqueous solution (2×60 mL), separated, dried, evaporated and re-crystallized from ethyl acetate and hexanes to give 6-bromo-2-(3-hydroxyphenyl)amino-N-(5-methyl-3-phenylisoxazol-4-yl)-4-quinolinecarboxamide (50 mg) as a yellow solid. $^1$H NMR (acetone-d$_6$): δ 2.53 (s, 3H), 6.72 (d, J=6.9 Hz, 1H), 7.15 (d, J=7.8 Hz, 1H), 7.26 (t, J=7.8 Hz, 1H), 7.51 (m, 4H), 7.60 (s, 1H), 7.78 (m, 3H), 7.87 (d, J=9.0 Hz, 1H), 8.15 (d, J=2.1 Hz, 1H), 8.70 (br, 1H), 9.77 (br, 1H); LCMS: ret. time: 25.49 min.; purity: 1100%; MS (m/e): 514.91 (M+).

The compounds listed in Table 1 were prepared by the methods described above. The compounds were characterized by their physical properties listed as follows:

Compound 1: LCMS: ret. time: 26.57 min.; purity: 95.33%; MS (m/e): 343.99 (M+H+).

Compound 3: LCMS: ret. time: 21.13 min.; purity: 100%; MS (m/e): 344.07 (M+H+).

Compound 5: LCMS: ret. time: 23.74 min.; purity: 100%; MS (m/e): 330.97 (M+H+).

Compound 7: LCMS: ret. time: 32.14 min.; purity: 98.20%; MS (m/e): 364.78 (M+H+).

Compound 9: LCMS: ret. time: 23.10 min.; purity: 100%; MS (m/e): 345.02 (M+H+).

Compound 11:LCMS: ret. time: 25.31 min.; purity: 95.61%; MS (m/e): 362.96(M+H+).

Compound 13: LCMS: ret. time: 35.11 min.; purity: 99.43%; MS (m/e): 398.93 (M+H+).

Compound 15: LCMS: ret. time: 35.07 min.; purity: 95.72%; MS (m/e): 399.29 (M+H+).
Compound 17: LCMS: ret. time: 37.50 min.; purity: 100%.
Compound 19: LCMS: ret. time: 32.61 min.; purity: 98.35%; MS (m/e): 402.97 (M+H+).
Compound 21: LCMS: ret. time: 19.66 min.; purity: 100%; MS (m/e): 301.06 (M+H+).
Compound 23: LCMS: ret. time: 26.70 min.; purity: 100%; MS (m/e): 414.95 (M+H+).
Compound 25: LCMS: ret. time: 26.23 min.; purity: 95.76%; MS (m/e): 396.90 (M+H+).
Compound 27: LCMS: ret. time: 21.45 min.; purity: 81.35%; MS (m/e): 482.76(M+H+).
Compound 29: LCMS: ret. time: 20.65 min.; purity: 89.06%; MS (m/e): 420.31 (M+H+).
Compound 31: LCMS: ret. time: 21.63 min.; purity: 84.95%; MS (m/e): 534.82 (M+H+).
Compound 33: LCMS: ret. time: 21.81 min.; purity: 73.31%; MS (m/e): 516.62 (M+H+).
Compound 35: LCMS: ret. time: 34.04 min.; purity: 98.90%; MS (m/e): 398.69 (M+H+).
Compound 37: LCMS: ret. time: 30.73 min.; purity: 100%; MS (m/e): 336.92 (M+H+).
Compound 39: LCMS: ret. time: 35.51 min.; purity: 99.91%; MS (m/e): 450.66 (M+H+).
Compound 41: LCMS: ret. time: 35.15 min.; purity: 96.21%; MS (m/e): 432.84 (M+H+).
Compound 43: LCMS: ret. time: 32.23 min.; purity: 100%; MS (m/e): 441.82 (M+H+).
Compound 45: LCMS: ret. time: 27.89 min.; purity: 96.80%; MS (m/e): 381.79 (M+H+).
Compound 47: LCMS: ret. time: 21.32 min.; purity: 99.44%; MS (m/e): 362.06 (M+H+).
Compound 49: LCMS: ret. time: 15.36 min.; purity: 93.52%; MS (m/e): 300.10 (M+H+).
Compound 51: LCMS: ret. time: 32.68 min.; purity: 96.80%; MS (m/e): 414.98 (M+H+).
Compound 53: LCMS: ret. time: 34.06 min.; purity: 100%; MS (m/e): 449.26 (M+H+).
Compound 57: LCMS: ret. time: 34.39 min.; purity: 98.83%; MS (m/e): 466.83 (M+H+).
Compound 61: LCMS: ret. time: 31.35 min.; purity: 100%; MS (m/e): 406.04 (M+H+).
Compound 63: LCMS: ret. time: 20.11 min.; purity: 100%; MS (m/e): 330.04 (M+H+).
Compound 65: LCMS: ret. time: 25.41 min.; purity: 100%; MS (m/e): 537.86 (M+H+).
Compound 67: LCMS: ret. time: 21.22 min.; purity: 96.94%; MS (m/e): 436.84 (M+H+).
Compound 69: LCMS: ret. time: 21.57 min.; purity: 100%; MS (m/e): 493.85 (M+H+).
Compound 71: LCMS: ret. time: 25.49 min.; purity: 100%; MS (m/e): 514.91 (M+H+).
Compound 73: LCMS: ret. time: 27.10 min.; purity: 100%; MS (m/e): 556.91 (M+H+).

7.7 The quinoline Compounds of the Invention Inhibit IgE-Induced Degranulation in Cellular Assays The ability of the quinoline compounds of the invention to inhibit IgE-induced degranulation was demonstrated in a variety of cellular assays with cultured human mast cells (CHMC) and can be measured by mouse bone marrow derived cells (BMMC). Inhibition of degranulation was measured at both low and high cell density by quantifying the release of the granule specific factors tryptase, histamine and hexosaminidase. Inhibition of release and/or synthesis of lipid mediators was assessed by measuring the release of leukotriene LTC4 and inhibition of release and/or synthesis of cytokines was monitored by quantifying TNF-α, IL-6 and IL-13. Tryptase and hexosaminidase were quantified using fluorogenic substrates as described in their respective examples. Histamine, TNFα, IL-6, IL-13 and LTC4 were quantified using the following commercial ELISA kits: histamine (Immunotech #2015, Beckman Coulter), TNFα (Biosource #KHC3011), IL-6 (Biosource #KMC0061), IL-13 (Biosource #KHC0132) and LTC4 (Cayman Chemical #520211). The protocols of the various assays are provided below.

7.7.1 Culturing of Human Mast and Basophil Cells

Human mast and basophil cells were cultured from CD34-negative progenitor cells as described below (see also the methods described in copending U.S. application Ser. No. 10/053,355, filed Nov. 8, 2001, the disclosure of which is incorporated herein by reference).

7.7.1.1 Preparation of STEMPRO-34 Complete Medium

To prepare STEMPRO-34 complete medium ("CM"), 250 mL STEMPRO-34™ serum free medium ("SFM"; Gibco-BRL, Catalog No. 10640) was added to a filter flask. To this was added 13 mL STEMPRO-34 Nutrient Supplement ("NS"; GibcoBRL, Catalog No. 10641) (prepared as described in more detail, below). The NS container was rinsed with approximately 10 mL SFM and the rinse added to the filter flask. Following addition of 5 mL L-glutamine (200 mM; Mediatech, Catalog No. MT 25-005-CI and 5 mL 100× penicillin/streptomycin ("pen-strep"; HyClone, Catalog No. SV30010), the volume was brought to 500 mL with SFM and the solution was filtered.

The most variable aspect of preparing the CM is the method by which the NS is thawed and mixed prior to addition to the SFM. The NS should be thawed in a 37° C. water bath and swirled, not vortexed or shaken, until it is completely in solution. While swirling, take note whether there are any lipids that are not yet in solution. If lipids are present and the NS is not uniform in appearance, return it to the water bath and repeat the swirling process until it is uniform in appearance. Sometimes this component goes into solution immediately, sometimes after a couple of swirling cycles, and sometimes not at all. If, after a couple of hours, the NS is still not in solution, discard it and thaw a fresh unit. NS that appears non-uniform after thaw should not be used.

7.7.1.2 Expansion of CD34+ Cells

A starting population of CD34-positive (CD34+) cells of relatively small number ($1-5\times10^6$ cells) was expanded to a relatively large number of CD34-negative progenitor cells (about $2-4\times10^9$ cells) using the culture media and methods described below. The CD34+ cells (from a single donor) were obtained from Allcells (Berkeley, Calif.). Because there is a degree of variation in the quality and number of CD34+ cells that Allcells typically provides, the newly delivered cells were transferred to a 15 mL conical tube and brought up to 10 mL in CM prior to use.

On day 0, a cell count was performed on the viable (phase-bright) cells and the cells were spun at 1200 rpm to pellet. The cells were resuspended to a density of 275,000 cells/mL with CM containing 200 ng/mL recombinant human Stem Cell Factor ("SCF"; Peprotech, Catalog No. 300-07) and 20 ng/mL human flt-3 ligand (Peprotech, Catalog No. 300-19) ("CM/SCF/flt-3 medium"). On about day 4 or 5, the density of the culture was checked by performing a cell count and the culture was diluted to a density of 275,000 cells/mL with fresh CM/SCF/flt-3 medium. On about day 7, the culture was transferred to a sterile tube and a cell count was performed. The cells were spun at 1200 rpm and resuspended to a density of 275,000 cells/mL with fresh CM/SCF/flt-3 medium.

This cycle was repeated, starting from day 0, a total of 3-5 times over the expansion period.

When the culture is large and being maintained in multiple flasks and is to be resuspended, the contents of all of the flasks are combined into a single container prior to performing a cell count. This ensures that an accurate cell count is achieved and provides for a degree of uniformity of treatment for the entire population. Each flask is checked separately for contamination under the microscope prior to combining to prevent contamination of the entire population.

Between days 17-24, the culture can begin to go into decline (i.e., approximately 5-10% of the total number of cells die) and fail to expand as rapidly as before. The cells are then monitored on a daily basis during this time, as complete failure of the culture can take place in as little as 24 hours. Once the decline has begun, the cells are counted, spun down at 850 rpm for 15 minutes, and resuspended at a density of 350,000 cells/mL in CM/SCF/flt-3 medium to induce one or two more divisions out of the culture. The cells are monitored daily to avoid failure of the culture.

When greater than 15% cell death is evident in the progenitor cell culture and some debris is present in the culture, the CD34-negative progenitor cells are ready to be differentiated.

7.7.1.3 Differentiation of CD34-Negative Progenitor Cells into Mucosal Mast Cells A second phase is performed to convert the expanded CD34-negative progenitor cells into differentiated mucosal mast cells. These mucosal cultured human mast cells ("CHMC") are derived from CD34+ cells isolated from umbilical cord blood and treated to form a proliferated population of CD34-negative progenitor cells, as described above. To produce the CD43-negative progenitor cells, the resuspension cycle for the culture was the same as that described above, except that the culture was seeded at a density of 425,000 cells/mL and 15% additional media was added on about day four or five without performing a cell count. Also, the cytokine composition of the medium was modified such that it contained SCF (200 ng/mL) and recombinant human IL-6 (200 ng/mL; Peprotech, Catalog No. 200-06 reconstituted to 100 ug/mL in sterile 10 mM acetic acid) ("CM/SCF/IL-6 medium").

Phases I and II together span approximately 5 weeks. Some death and debris in the culture is evident during weeks 1-3 and there is a period during weeks 2-5 during which a small percentage of the culture is no longer in suspension, but is instead attached to the surface of the culture vessel.

As during Phase I, when the culture is to be resuspended on day seven of each cycle, the contents of all flasks are combined into a single container prior to performing a cell count to ensure uniformity of the entire population. Each flask is checked separately for contamination under the microscope prior to combining to prevent contamination of the entire population.

When the flasks are combined, approximately 75% of the volume is transferred to the communal container, leaving behind about 10 mL or so in the flask. The flask containing the remaining volume was rapped sharply and laterally to dislodge the attached cells. The rapping was repeated at a right angle to the first rap to completely dislodge the cells.

The flask was leaned at a 45 degree angle for a couple of minutes before the remaining volume was transferred to the counting vessel. The cells were spun at 950 rpm for 15 min prior to seeding at 35-50 mL per flask (at a density of 425,000 cells/mL).

7.7.1.4 Differentiation of CD34-Negative Progenitor Cells into Connective Tissue-Type Mast Cells A proliferated population of CD34-negative progenitor cells is prepared as above and treated to form a tryptase/chymase positive (connective tissue) phenotype. The methods are performed as described above for mucosal mast cells, but with the substitution of IL-4 for IL-6 in the culture medium. The cells obtained are typical of connective tissue mast cells.

7.7.1.5 Differentiation of CD34-Negative Progenitor Cells into Basophil Cells

A proliferated population of CD34-negative progenitor cells is prepared as described in Section 7.7.1.3, above, and used to form a proliferated population of basophil cells. The CD34-negative cells are treated as described for mucosal mast cells, but with the substitution of IL-3 (at 20-50 ng/mL) for IL-6 in the culture medium.

7.7.2 CHMC Low Cell Density IgE Activation: Tryptase and LTC4 Assays

To duplicate 96-well U-bottom plates (Costar 3799) add 65 ul of compound dilutions or control samples that have been prepared in MT [137 mM NaCl, 2.7 mM KCl, 1.8 mM $CaCl_2$, 1.0 mM $MgCl_2$, 5.6 mM Glucose, 20 mM Hepes (pH 7.4), 0.1% Bovine Serum Albumin, (Sigma A4503)] containing 2% MeOH and 1% DMSO. Pellet CHMC cells (980 rpm, 10 min) and resuspend in pre-warmed MT. Add 65 ul of cells to each 96-well plate. Depending on the degranulation activity for each particular CHMC donor, load 1000-1500 cells/well. Mix four times followed by a 1 hr incubation at 37° C. During the 1 hr incubation, prepare 6× anti-IgE solution [rabbit anti-human IgE (1 mg/ml, Bethyl Laboratories A80-109A) diluted 1:167 in MT buffer]. Stimulate cells by adding 25 ul of 6× anti-IgE solution to the appropriate plates. Add 25 ul MT to un-stimulated control wells. Mix twice following addition of the anti-IgE. Incubate at 37° C. for 30 minutes. During the 30 minute incubation, dilute the 20 mM tryptase substrate stock solution [(Z-Ala-Lys-Arg-AMC2TFA; Enzyme Systems Products, #AMC-246)] 1:2000 in tryptase assay buffer [0.1 M Hepes (pH 7.5), 10% w/v Glycerol, 10 uM Heparin (Sigma H-4898) 0.01% $NaN_3$]. Spin plates at 1000 rpm for 10 min to pellet cells. Transfer 25 ul of supernatant to a 96-well black bottom plate and add 100 ul of freshly diluted tryptase substrate solution to each well. Incubate plates at room temperature for 30 min. Read the optical density of the plates at 355 nm/460 nm on a spectrophotometric plate reader.

Leukotriene C4 (LTC4) is also quantified using an ELISA kit on appropriately diluted supernatant samples (determined empirically for each donor cell population so that the sample measurement falls within the standard curve) following the supplier's instructions.

7.7.3 CHMC High Cell Density IgE Activation: Degranulation (Tryptase, Histamine), Leukotriene (LTC4), and Cytokine (TNFalpha, IL-13) Assays Cultured human mast cells (CHMC) are sensitized for 5 days with IL-4 (20 ng/ml), SCF (200 ng/ml), IL-6 (200 ng/ml), and Human IgE (CP 1035K from Cortx Biochem, 100-500 ng/ml depending on generation) in CM medium. After sensitizing, cells are counted, pelleted (1000 rpm, 5-10 minutes), and resuspended at 1-2×10⁶ cells/ml in MT buffer. Add 100 ul of cell suspension to each well and 100 ul of compound dilutions. The final vehicle concentration is 0.5% DMSO. Incubate at 37° C. (5% $CO_2$) for 1 hour. After 1 hour of compound treatment, stimulate cells with 6× anti-IgE. Mix wells with the cells and allow plates to incubate at 37° C. (5% $CO_2$) for one hour. After 1 hour incubation, pellet cells (10 minutes, 1000 RPM) and collect 200 ul per well of the supernatant, being careful not to disturb pellet. Place the supernatant plate on ice. During the 7-hour step (see next) perform tryptase assay on supernatant that had been diluted 1:500. Resuspend cell pellet in 240 ul of CM media containing 0.5% DMSO and corresponding concentration of compound. Incubate CHMC cells for 7 hours at 37° C. (5% $CO_2$). After incubation, pellet cells (1000 RPM, 10 minutes) and collect 225 ul per well and place in −80° C. until ready to perform ELISAS. ELISAS are performed on appropriately diluted samples (determined empirically for each donor cell population so that the sample measurement falls within the standard curve) following the supplier's instructions.

7.7.4 BMMC High Cell Density IgE Activation: Degranulation (Hexosiminidase, Histamine), Leukotriene (LTC4), and Cytokine (TNFalpha, IL-6) Assays 7.7.4.1 Preparation of WEHI-Conditioned Medium WEHI-conditioned medium was obtained by growing murine myelomonocytic WEHI-3B cells (American Type Culture Collection, Rockville, Md.) in Iscove's Modified Eagles Media (Mediatech, Hernandon, Va.) supplemented with 10% heat-inactivated fetal bovine serum (FBS; JRH Biosciences, Kansas City, Mo.), 50 µM 2-mercaptoethanol (Sigma, St. Louis, Mo.) and 100 IU/mL penicillin-steptomycin (Mediatech) in a humidified 37° C., 5% $CO_2$/95% air incubator. An initial cell suspension was seeded at 200,000 cells/mL and then split 1:4 every 3-4 days over a period of two weeks. Cell-free supernatants were harvested, aliquoted and stored at −80° C. until needed.

7.7.4.2 Preparation of BMMC Medium

BMMC media consists of 20% WEHI-conditioned media, 10% heat-inactivated FBS (JHR Biosciences), 25 mM HEPES, pH7.4 (Sigma), 2 mM L-glutamine (Mediatech), 0.1 mM non-essential amino acids (Mediatech), 1 mM sodium pyruvate (Mediatech), 50 µM 2-mercaptoethanol (Sigma) and 100 IU/mL penicillin-streptomycin (Mediatech) in RPMI 1640 media (Mediatech). To prepare the BMMC Media, all components are added to a sterile IL filter unit and filtered through a 0.2 µm filter prior to use.

7.7.4.3 Protocol

Bone marrow derived mast cells (BMMC) are sensitized overnight with murine SCF (20 ng/ml) and monoclonal anti-DNP (10 ng/ml, Clone SPE-7, Sigma # D-8406) in BMMC media at a cell density of 666×10³ cells/ml. After sensitizing, cells are counted, pelleted (1000 rpm, 5-10 minutes), and resuspended at 1-3×10⁶ cells/ml in MT buffer. Add 100 ul of cell suspension to each well and 100 ul of compound dilutions. The final vehicle concentration is 0.5% DMSO. Incubate at 37° C. (5% $CO_2$) for 1 hour. After 1 hour of compound treatment, stimulate cells with 6× stimulus (60 ng/ml DNP-BSA). Mix wells with the cells and allow plates to incubate at 37° C. (5% $CO_2$) for one hour. After 1 hour incubation, pellet cells (10 minutes, 1000 RPM) and collect 200 ul per well of the supernatant, being careful not to disturb pellet, and transfer to a clean tube or 96-well plate. Place the supernatant plate on ice. During the 4-5 hour step (see next) perform the hexosiminidase assay. Resuspend cell pellet in 240 ul WEI-conditioned media containing 0.5% DMSO and corresponding concentration of compound. Incubate BMMC cells for 4-5 hours at 37° C. (5% $CO_2$). After incubation, pellet cells (1000 RPM, 10 minutes) and collect 225 ul per well and place in −80° C. until ready to perform ELISAS. ELISAS can be performed on appropriately diluted samples (determined empirically for each donor cell population so that the sample measurement falls within the standard curve) following the supplier's instructions.

Hexosaminidase assay: In a solid black 96-well assay plate, add 50 uL hexosaminidase substrate (4-methylumbelliferyl-N-acetyl-β-D-glucosaminide; 2 mM) to each well. Add 50 uL of BMMC cell supernatant (see above) to the hexoseaminidase substrate, place at 37° C. for 30 minutes and read the plate at 5, 10, 15, and 30 minutes on a spectrophotometer.

7.7.5 Basophil IgE or Dustmite Activation: Histamine Release Assay

The basophil activation assay was carried out using whole human peripheral blood from donors allergic to dust mites with the majority of the red blood cells removed by dextran sedimentation. Human peripheral blood was mixed 1:1 with 3% dextran T500 and RBCs were allowed to settle for 20-25 min. The upper fraction was diluted with 3 volumes of D-PBS and cells were spun down for 10 min at 1500 rpm, RT. Supernatant was aspirated and cells were washed in an equal volume MT-buffer. Finally, cells were resuspended in MT-buffer containing 0.5% DMSO in the original blood volume. 80 uL cells were mixed with 20 uL compound in the presence of 0.5% DMSO, in triplicate, in a V-bottom 96-well tissue culture plate. A dose range of 8 compound concentrations can be tested resulting in a 10-point dose response curve including maximum (stimulated) and minimum (unstimulated) response. Cells were incubated with compound for 1 hour at 37° C., 5% $CO_2$ after which 20 uL of 6× stimulus [1 ug/mL anti-IgE (Bethyl Laboratories) 667 au/mL house dustmite (Antigen Laboratories)] was added. The cells were stimulated for 30 minutes at 37° C., 5% $CO_2$. The plate was spun for 10 min at 1500 rpm at room temperature and 80 uL the supernatant was harvested for histamine content analysis using the histamine ELISA kit supplied by Immunotech. The ELISA can be performed according to supplier's instructions.

7.7.6 Results

The results of low density CHMC assays (Section 7.7.2) and CHMC iono (Section 7.8.1) are provided in TABLE 1. In TABLE 1, a value of "+" indicates an $IC_{50}$ of 10 µM or less, in the specified assay; a value of "−" indicates an $IC_{50}$ of greater than 10 µM in the specified assay. Most compounds tested had $IC_{50}$s of less than 10 µM, with many exhibiting $IC_{50}$s in the sub-micromolar range.

TABLE 1

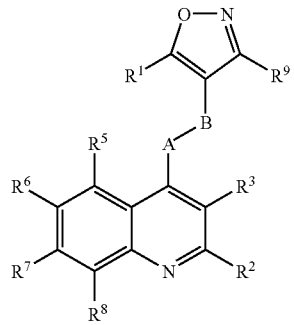

| Cmpd | CHMC IGE/CHMC-IONO | R¹ | A | B | R² | R³ | R⁵ | R⁶ | R⁷ | R⁸ | R⁹ |
|---|---|---|---|---|---|---|---|---|---|---|---|
| 1 | −/− | Me | CO | NH | Ph | H | H | H | H | H | Me |
| 3 | − | Me | NH | CO | Me | H | H | H | H | H | Ph |
| 5 | +/+ | Me | O | CO | H | H | H | H | H | H | Ph |
| 7 | +/+ | Me | O | CO | H | H | H | H | Cl | H | Ph |
| 9 | +/+ | Me | O | CO | Me | H | H | H | H | H | Ph |
| 11 | +/+ | Me | O | CO | Me | H | H | F | H | H | Ph |
| 13 | +/+ | Me | O | CO | H | H | H | H | CF₃ | H | Ph |
| 15 | + | Me | O | CO | H | H | H | H | H | CF₃ | Ph |
| 17 | +/+ | Me | O | CO | H | COOEt Et | H | H | CF₃ | H | Ph |
| 19 | +/+ | Me | O | CO | COOEt | H | H | H | H | H | Ph |
| 21 | + | Me | O | CO | Me | H | H | F | H | H | Me |
| 23 | + | Me | O | CO | Me | H | H | F | H | H | 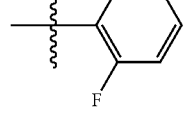 |
| 25 | +/+ | Me | O | CO | Me | H | H | F | H | H | 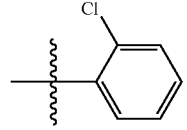 |
| 27 | +/+ | Me | O | CO | CF₃ | H | H | OCF₃ | H | H | Ph |
| 29 | +/+ | Me | O | CO | CF₃ | H | H | OCF₃ | H | H | Me |
| 31 | +/+ | Me | O | CO | CF₃ | H | H | OCF₃ | H | H | 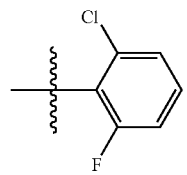 |
| 33 | + | Me | O | CO | CF₃ | H | H | OCF₃ | H | H | 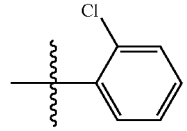 |
| 35 | +/+ | Me | NH | CO | H | H | H | H | CF₃ | H | Ph |
| 37 | −/− | Me | NH | CO | H | H | H | H | CF₃ | H | Me |
| 39 | +/30 | Me | NH | CO | H | H | H | H | CF₃ | H | 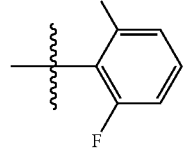 |

TABLE 1-continued

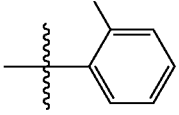

| Cmpd | CHMC IGE/CHMC -IONO | R¹ | A | B | R² | R³ | R⁵ | R⁶ | R⁷ | R⁸ | R⁹ |
|---|---|---|---|---|---|---|---|---|---|---|---|
| 41 | −/− | Me | NH | CO | H | H | H | H | CF₃ | H | 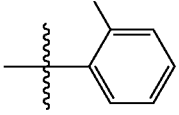 |
| 43 | +/− | Me | CO | NH | Cl | H | H | Br | H | H | Ph |
| 45 | +/− | Me | CO | NH | Cl | H | H | Br | H | H | Me |
| 47 | +/− | Me | CO | NH | Me | H | H | F | H | H | Ph |
| 49 | +/− | Me | CO | NH | Me | H | H | F | H | H | Me |
| 51 | +/+ | Me | O | CO | H | H | H | OCF₃ | H | H | Ph |
| 53 | +/+ | Me | O | CO | H | H | H | OCF₃ | H | H | 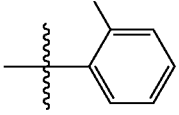 |
| 57 | +/− | Me | O | CO | H | H | H | OCF₃ | H | H | 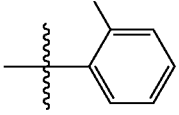 |
| 61 | −/− | Me | CO | NH | Ph | H | H | H | H | H | Ph |
| 63 | −/− | Me | CO | NH | H | H | H | H | H | H | Ph |
| 65 | +/− | Me | CO | NH | 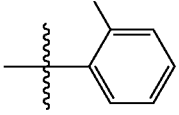 | H | H | Br | H | H | Ph |
| 67 | +/− | Me | CO | NH | —NHCH₃ | H | H | Br | H | H | Ph |
| 69 | −/− | Me | CO | NH | 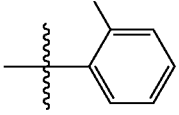 | H | H | Br | H | H | Ph |
| 71 | +/+ | Me | CO | NH | 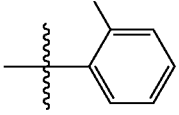 | H | H | Br | H | H | Ph |

TABLE 1-continued

| Cmpd | CHMC IGE/CHMC -IONO | R¹ | A | B | R² | R³ | R⁵ | R⁶ | R⁷ | R⁸ | R⁹ |
|------|---------------------|----|---|---|----|----|----|----|----|----|----|
| 73 | -/- | Me | CO | NH | (2,3-dihydro-1,4-benzodioxin-6-ylamino) | H | H | Br | H | H | Ph |

7.8 The quinoline Compounds of the Invention Selectively Inhibit the Upstream IgE Receptor Cascade To confirm that many of the quinoline compounds of the invention exert their inhibitory activity by blocking or inhibiting the early IgE receptor signal transduction cascade, many of the compounds were tested in cellular assays for ionomycin-induced degranulation, as described below.

7.8.1 CHMC Low Cell Density Ionomycin Activation: Tryptase Assay

Assays for ionomycin-induced mast cell degranulation were carried out as described for the CHMC Low Density IgE Activation assays (Section 7.7.2, supra), with the exception that during the 1 hour incubation, 6× ionomycin solution [5 mM ionomycin (Signma 1-0634) in MeOH (stock) diluted 1:416.7 in MT buffer (2 μM final)] was prepared and cells were stimulated by adding 25 μl of the 6× ionomycin solution to the appropriate plates.

7.8.2 Basophil Ionomycin Activation: Histamine Release Assay

Assays for ionomycin-induced basophil cell degranulation can be carried out as described for the Basophil IgE or Dust-mite Activation Assay (Section 7.7.5, supra), with the exception that following incubation with compound, cells were stimulated with 20 μl of 2 μM ionomycin.

7.8.3 Results

The results of the ionomycin-induced degranulation assays, reported as $IC_{50}$ values (in μM) are provided in TABLE 1, supra. Of the active compounds tested (i.e., those that inhibit IgE-induced degranulation), the vast majority inhibit ionomycin-induced degranulation, confirming that these active compounds selectively inhibit the later (or downstream) IgE receptor signal transduction cascade.

These results were confirmed for certain compounds by measuring anti-IgE-induced and ionomycin-induced calcium ion flux in CHMC cells.

7.9 The Inhibitory Effect of the Quinoline Compounds of the Invention is Immediate To test the immediacy of their inhibitory effect, certain quinolines of the invention can be added simultaneously with anti-IgE antibody activator in the cellular assays described above. All compounds can be tested to determine whether they block IgE-induced degranulation of CHMC cells to the same extent as when the compounds are pre-incubated with CHMC cells for 10 or 30 min. prior to receptor cross-linking.

7.10 Kinetics of Pharmacological Activity In Vitro

Compounds of the invention can be tested in washout experiments. In the experiments, CHMC cells can be activated immediately with anti-IgE antibody in the presence of 1.25 μM compound (time zero), or the compound can be washed out followed by activation with anti-IgE antibody at 30, 60 or 120 min.

7.11 Toxicity: T- and B-Cells

The ability of the compounds of the invention to exert their inhibitor activity without being toxic to cells of the immune system can be demonstrated in cellular assays with B- and T-cells. The protocols for the assays are provided below.

7.11.1 Jurkat (T-Cell) Toxicity

Dilute Jurkat cells to $2 \times 10^5$ cells/ml in complete RPMI (10% heat-inactivated fetal bovine serum) media and incubate at 37° C., 5% $CO_2$ for 18 hours. Add 65 ul cells at $7.7 \times 10^5$ cells/ml to a 96-well V-bottom plate (TC-treated, Costar) containing 65 ul 2×compound (final vehicle concentration is 0.5% DMSO, 1.5% MeOH). Mix, incubate plates for 18-24 hr at 37° C., 5% $CO_2$. Toxicity can be assessed by flow cytometric analysis of cellular light scatter.

7.11.2 BJAB (B-Cell) Toxicity

The B-cell line BJAB was cultured in log phase in RPMI1640+10% heat-inactivated fetal bovine serum, 1× L-glutamine, 1× penicillin, 1× streptavidin and 1× beta-mercaptoethanol at 37° C., 5% CO2. First, BJABs were harvested, spun and resuspended in culture medium to a concentration of $7.7 \times 10^5$ cells/mL. 65 uL cells can be mixed with 65 uL compound, in duplicate and in the presence of 0.1% DMSO in a V-bottomed 96-well tissue culture plate. Cells can be incubated with compound at various dilutions at 37° C., 5% $CO_2$. Toxicity can be assessed by flow cytometric analysis of cellular light scatter.

7.11.3 Toxicity: Cell Titer Glo Assay

Seed 50 μl cells ($1 \times 10^6$/ml) into each well containing 50 μl compound. The final vehicle concentration should be 0.5%

DMSO, 1.5% MeOH. Shake plates for 1 minute to mix cells and compound. Incubate plates at 37° C. (5% $CO_2$) for 18 hours. Next day, harvest 50 µl cells from each well, add to 50 µl Cell Titer Glo reagent (Invitrogen). Shake plates for 1 minute. Read on luminometer.

7.12 The Compounds Can be Effective for the Treatment of Allergies

The in vivo efficacy of the quinoline compounds of the invention, and towards allergies can be evaluated in the mouse model of passive cutaneous anaphylaxis (PCA). This model provides a direct measure of IgE-induced degranulation of tissue mast cells. In this model, IgE primed animals are exposed to an allergen challenge and the change in permeability of dermal vasculature that results from histamine release from mast cells is measured by change in the amount of dye leakage into surrounding tissue. Inhibition of mediator release by compounds that modulate mast cell degranulation is easily measured by extracting the dye from the tissue.

7.12.1 Study Protocol and Results

In the PCA assay mice are passively sensitized by intradermal injection with anti-dinitrophenol (DNP) IgE antibodies (Day-1). At predetermined times (5-60 minutes prior to challenge), animals are treated with the test agent (Day 0). The modulatory effect of the agent on cutaneous mast cell degranulation is measured following intravenous injection of DNP conjugated to human serum albumin (HSA-DNP), together with Evans blue dye. The resulting cross-linking of the IgE receptor and subsequent mast cell degranulation-induced increase in vascular permeability is determined by measuring the amount of dye extravasation into the tissue. Dye is extracted from the tissue by formamide, and the absorbance of this extract is read at 620 nm. The inhibitory effect of drug treatment is reported as the percent inhibition compared to vehicle treatment, that is, the percent reduction in $A_{620}$.

Two compounds have been tested as positive controls: the histamine antagonist diphenhydramine and the serotonin antagonist cyproheptadine. Both mediators (histamine and serotonin) are released upon IgE-mediated degranulation from the mouse mast cell. This is in contrast to human mast cells, which do not contain any serotonin. Dose response curve with diphenhydramine shows an inhibition of the PCA response up to 86% with the highest dose (50 mg/kg, i.p., 30 minutes pretreatment time). This high dose however was not well tolerated by the animals. For this reason, cyproheptadine was used as a positive control. Cyproheptadine inhibited the PCA response by 61% +/−4% (8 mg/kg, i.p., 30 minutes pretreatment time, n=23 experiments).

7.12.2 Study Protocol

In the sheep model of allergic asthma, sheep can be administered aerosols of test article via an endotracheal tube, followed by an aerosol challenge with antigen extracted from the roundworm, Ascaris suum, to which the sheep are naturally allergic. Allergen challenge leads to direct bronchoconstriction [early asthmatic response (EAR), and late asthmatic response (LAR)], and a persistent non-specific airway hyperresponsiveness (AHR). These three characteristics are similar to those seen in human allergic asthmatics. The activity of the test agent can be determined by changes in the lung resistance ($R_L$), which is calculated from measurements of transpulmonary pressure, flow, and respiratory volume. The historical control data obtained from the same sheep following saline treatment and allergen challenge show a sharp increase of $R_L$ during the EAR that persists for approximately 2-3 hours following antigen challenge. The LAR is a less pronounced increase in $R_L$, which starts from 5-6 hours following antigen challenge and is resolved by 8 hours post-challenge. Twenty-four hours after the challenge a dose response to carbachol is measured to determine the AHR, which is expressed as the dose of carbachol required to increase $R_L$ by 400% over baseline. (This measurement is referred to as the provocative concentration of carbachol that elicits a 400% increase in RL over baseline ($PC_{400}$). The data can be compared to historical control data for the same individual when administered a saline control aerosol and challenged with Ascaris suum.

7.13 Toxicity and Pharmacokinetics

The non-toxicity of the quinolines can be demonstrated using standard animal models, as described below.

7.13.1 Mouse 7-Day Repeated Dose Subcutaneous Administration Tolerance Study In this study, female BALB/c® mice can be treated by subcutaneous administration with either vehicle or test article formulation once daily for 7 days to determine the subcutaneous administration tolerability of a particular compound. The study consists of four toxicology groups as follows: mice in two separate drug-treated groups (of nine mice each) can be administered 30 mg/ml of a compound in a CMC suspension (50 mM phosphate buffer, pH7, with 0.1% (w/v) carboxymethyl cellulose) or a 67% PEG 400 solution (67% PEG 400/33% 50 mM citrate) at doses of 200 mg/kg/day and mice in two separate vehicle control groups (of six mice each) receive either 0.9% sodium chloride or 67% PEG 400 solution. The administered dose volume should be 6.7 ml/kg/day for all four groups of mice. Six mice in each of the drug-treated groups serve as toxicokinetic satellite animals (3 per group per timepoint) for toxicokinetic evaluation of parent and major metabolite (MM) levels at 24 hours after the first and seventh dose. Skin from the dose site can be collected and evaluated for microscopic changes.

7.13.2 Mouse 14-Day Repeated Dose Oral Toxicology Study

In this dose-ranging toxicology and toxicokinetics study, BALB/c mice can be treated by oral gavage with either vehicle only or test article formulation once daily for 14 days. The study consists of four toxicology groups of five mice per sex and four toxicokinetic satellite groups receiving the same treatment regimen in parallel. Vehicle control mice receive either 6.7 ml/kg/day or 16.7 ml/kg/day of a 67% PEG 400, 33% 50 mM citrate (v/v) formulation. Animals that can be treated with a test article receive either a low dose of 200 mg/kg/day (6.7 ml/kg/day) or a high dose of 500 mg/kg/day (16.7 ml/kg/day) of the test compound, using a 30 mg/ml solution.

7.13.3 Rat 14-Day Repeated Dose Toxicity Study

In this dose-ranging toxicology and toxicokinetics study, Sprague Dawley rats can be treated by oral gavage with either vehicle only or test article formulation once daily for 14 days. The study consists of four toxicology groups of five rats per sex and two toxicokinetics satellite groups. Five rats per sex received either 6.7 ml/kg/day (low volume control) or 16.7 ml/kg/day (high volume control), of a 67% PEG 400 33% 50 mM citrate (v/v) vehicle formulation. Five male rats can receive the low dose of 200 mg/kg/day of test compound (6.7 ml/kg), and five rats per sex can receive the high dose of 500 mg/kg/day of test compound (16.7 ml/kg/day) using a 30 mg/ml solution.

Although the foregoing invention has been described in some detail to facilitate understanding, it will be apparent that certain changes and modifications may be practiced within the scope of the appended claims. Accordingly, the described embodiments are to be considered as illustrative and not restrictive, and the invention is not to be limited to the details given herein, but may be modified within the scope and equivalents of the appended claims.

All literature and patent references cited throughout the application are incorporated by reference into the application for all purposes.

What is claimed is:

1. A compound according to structural formula (I):

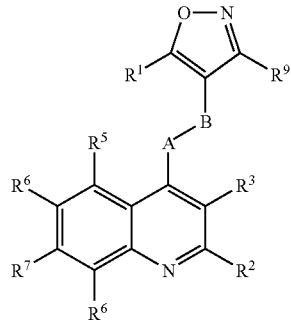

and a salt, hydrate, solvate or N-oxide thereof, wherein:
- $R^1$ is an alkyl group optionally substituted with one or more of the same or different $R^{10}$ groups;
- $R^2$, $R^3$, $R^5$, $R^6$, $R^7$ and $R^8$ are each, independently of one another, seleted from the group consisting of a hydrogen atom, $-OR^d$, $-SR^d$, (C1-C3) haloalkyloxy, (C1-C3) perhaloalkyloxy, $-NR^c$-aryl, $-NR^c$-heteroaryl, halogen, (C1-C3) haloalkyl, (C1-C3) perhaloalkyl, $-CF_3$, $-CH_2CF_3$, $-CF_2CF_3$, (C1-C6) alkyl optionally substituted with one or more of the same or different $R^{10}$ groups, (C5-C10) aryl optionally substituted with one or more of the same or different $R^{10}$ groups, phenyl optionally substituted with one or more of the same or different $R^{10}$ groups, and 5-10 membered heteroaryl optionally substituted with one or more of the same or different $R^{10}$ groups;
- $R^9$ is selected from the group consisting of (C1-C3) haloalkyl, (C1-C3) perhaloalkyl, $-CF_3$, $-CH_2CF_3$, $-CF_2CF_3$, (C1-C6) alkyl optionally substituted with one or more of the same or different $R^{10}$ groups, (C5-C10) aryl optionally substituted with one or more of the same or different $R^{10}$ groups, phenyl optionally substituted with one or more of the same or different $R^{10}$ groups;
- $R^{10}$ is selected from the group consisting of $R^a$, $R^b$, $R^a$ substituted with one or more of the same or different $R^a$ or $R^b$, $-OR^a$ substituted with one or more of the same or different $R^a$ or $R^b$, $-(CH_2)_m-R^b$, $-(CHR^a)_m-R^b$, $-O-(CH_2)_m-R^b$, $-S-(CH_2)_m-R^b$, and $-O-(CHR^a)_m-R^b$;
- each $R^a$ is independently selected from the group consisting of hydrogen, (C1-C6) alkyl, (C3-C8) cycloalkyl, cyclohexyl, (C4-C11) cycloalkylalkyl, (C5-C10) aryl, phenyl, (C6-C16) arylalkyl, benzyl;
- each $R^b$ is a suitable group independently selected from the group consisting of $-OR^d$, (C1-C3) haloalkyloxy, halogen, and $-CF_3$,
- each $R^c$ is independently a protecting group, $R^a$ or $R^a$ optionally substituted with one or more of the same or different $R^a$ or suitable $R^b$ groups;
- each $R^d$ is independently a protecting group, $R^a$ or $R^a$ optionally substituted with one or more of the same or different $R^a$ or suitable $R^b$ groups;
- each m is independently an integer from 1 to 3;
- A is NH or CO; and
- B is CO, NH or O, provided that one of A or B is C(O).

2. A compound according to structural formula (I):

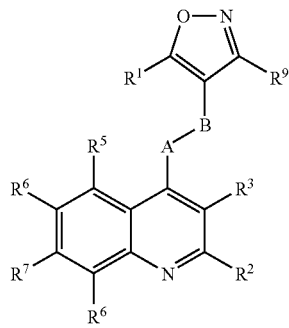

and a salt, hydrat; solvate or N-oxide thereof, wherein:
- $R^1$ is an alkyl group optionally substituted with one or more of the same or different $R^{10}$ groups;
- $R^2$, $R^3$, $R^5$, $R^6$, $R^7$ and $R^8$ are each, independently of one another, selected from the group consisting of hydrogen, $-OR^d$, $-SR^d$, (C1-C3) haloalkyloxy, (C1-C3) perhaloalkyloxy, $-NR^c$-aryl, $-NR$-heteroaryl, halogen, (C1-C3) haloalkyl, (C1-C3) perhaloalkyl, $-CF_3$, $-CH_2CF_3$, $-CF_2CF_3$, (C1-C6) alkyl optionally substituted with one or more of the same or different $R^{10}$ groups, (C5-C10) aryl optionally substituted with one or more of the same or different $R^{10}$ groups, phenyl optionally substituted with one or more of the same or different $R^{10}$ groups, and 5-10 membered heteroaryl optionally substituted with one or more of the same or different $R^{10}$ groups;
- $R^9$ is selected from the group consisting of (C1-C3) haloalkyl, (C1-C3) perhaloalkyl, $-CF_3$, $-CH_2CF_3$, $-CF_2CF_3$, (C1-C6) alkyl optionally substituted with one or more of the same or different $R^{10}$ groups, and phenyl optionally substituted with one or more of the same or different $R^{10}$ groups;
- $R^{10}$ is selected from the group consisting of $R^a$, $R^b$, $R^a$ substituted with one or more of the same or different $R^a$ or $R^b$, $-OR^a$ substituted with one or more of the same or different $R^a$ or $R^b$, $-(CH_2)_m-R^b$, $-(CHR^a)_m-R^b$, $-O-(CH_2)_m-R^b$, $-S-(CH_2)_m-R^b$, and -O-$(CHR^a)_m-R^b$;
- each $R^a$ is independently selected from the group consisting of hydrogen, (C1-C6) alkyl, (C3-C8) cycloalkyl, cyclohexyl, (C4-C11) cycloalkylalkyl, (C5-C10) aryl, phenyl, (C6-C16) arylalkyl, and benzyl;
- each $R^b$ is a suitable group independently selected from the group consisting of $-OR^d$, (C1-C3) haloalkyloxy, halogen, and $-CF_3$,
- each $R^c$ is independently a protecting group, $R^a$ or $R^a$ optionally substituted with one or more of the same or different $R^a$ or suitable $R^b$ groups;
- each $R^d$ is independently a protecting group, $R^a$ or $R^a$ optionally substituted with one or more of the same or different $R^a$ or suitable $R^b$ groups;
- each m is independently an integer from 1 to 3;
- A is NH or CO; and
- B is CO, NH or O, provided that one of A or B is CO.

3. The compound of claim 1 or claim 2 in which $R^1$ is a methyl group.

4. The compound of claim 1 in which $R^1$ is a methyl group and $R^9$ is a substituted or unsubstituted phenyl group.

5. The compound of claim 1 or claim 2 in which $R^1$ is a methyl group and $R^9$ is a substituted phenyl group.

6. The compound of claim 5 in which the substituted phenyl group is selected from the group consisting of 2-chlorophenyl and 2-chloro-6-fluorophenyl.

7. The compound of claim 1 or claim 2 in which $R^2$ is selected from the group consisting of hydrogen, phenyl, methyl, —$CO_2Et$, —$CF_3$, Cl, —$NHCH_3$,

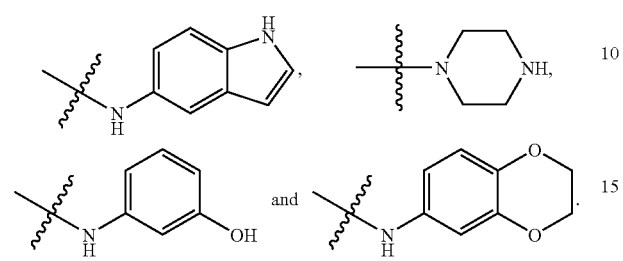

8. The compound of claim 1 or claim 2 in which $R^6$ is selected from the group consisting of hydrogen, F, —$OCF_3$, and Br.

9. The compound of claim 1 or claim 2 in which $R^7$ is selected from the group consisting of hydrogen, Cl and —$CF_3$.

10. The compound of claim 1 or claim 2 in which $R^1$ is a methyl group; $R^9$ is a substituted or unsubstituted phenyl group; $R^2$ is selected from the group consisting of hydrogen, phenyl, methyl, —$CO_2Et$, —$CF_3$, Cl, —$NHCH_3$,

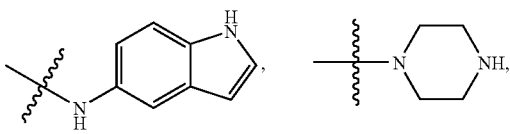

-continued

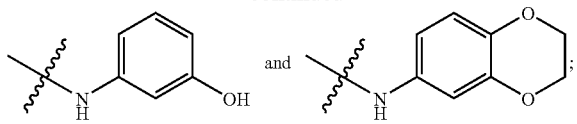

$R^6$ is selected from the group consisting of hydrogen, F, —$OCF_3$, and Br; and $R^7$ is selected from the group consisting of hydrogen, Cl and —$CF_3$.

11. A compound according to structural formula (I):

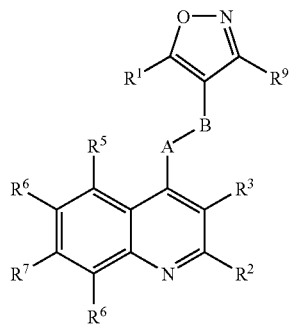

and a salt, hydrate, solvate or N-oxide thereof, in which A, B, $R^1$, $R^2$, $R^3$, $R^5$, $R^6$, $R^7$, $R^8$ and $R^9$ are selected from the group of substituent combinations delineated below:

| No. | A | B | $R^1$ | $R^2$ | $R^3$ | $R^5$ | $R^6$ | $R^7$ | $R^8$ | $R^9$ |
|---|---|---|---|---|---|---|---|---|---|---|
| 1 | CO | NH | Me | Ph | H | H | H | H | H | Me |
| 3 | NH | CO | Me | Me | H | H | H | H | H | Ph |
| 5 | O | CO | Me | H | H | H | H | H | H | Ph |
| 7 | O | CO | Me | H | H | H | H | Cl | H | Ph |
| 9 | O | CO | Me | Me | H | H | H | H | H | Ph |
| 13 | O | CO | Me | H | H | H | H | H | $Cf_3$ | H | Ph |
| 15 | O | CO | Me | H | H | H | H | H | $CF_3$ | Ph |
| 17 | O | CO | Me | H | COOEt | H | H | $CF_3$ | H | Ph |
| 19 | O | CO | Me | COOEt | H | H | H | H | H | Ph |
| 21 | O | CO | Me | Me | H | H | F | H | H | Me |
| 23 | O | CO | Me | Me | H | H | F | H | H |  |
| 25 | O | CO | Me | Me | H | H | F | H | H |  |
| 27 | O | CO | Me | $CF_3$ | H | H | $OCF_3$ | H | H | Ph |
| 29 | O | CO | Me | $CF_3$ | H | H | $OCF_3$ | H | H | Me |

-continued

| No. | A | B | R¹ | R² | R³ | R⁵ | R⁶ | R⁷ | R⁸ | R⁹ |
|---|---|---|---|---|---|---|---|---|---|---|
| 31 | O | CO | Me | CF₃ | H | H | OCF₃ | H | H | 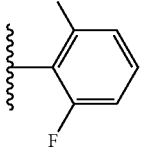 |
| 33 | O | CO | Me | CF₃ | H | H | OCF₃ | H | H | 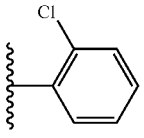 |
| 35 | NH | CO | Me | H | H | H | H | CF₃ | H | Ph |
| 37 | NH | CO | Me | H | H | H | H | CF₃ | H | Me |
| 39 | NH | CO | Me | H | H | H | H | CF₃ | H | 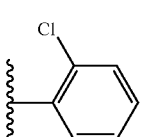 |
| 41 | NH | CO | Me | H | H | H | H | CF₃ | H | 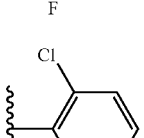 |
| 43 | CO | NH | Me | Cl | H | H | Br | H | H | Ph |
| 45 | CO | NH | Me | Cl | H | H | Br | H | H | Me |
| 47 | CO | NH | Me | Me | H | H | F | H | H | Ph |
| 49 | CO | NH | Me | Me | H | H | F | H | H | Me |
| 51 | O | CO | Me | H | H | H | OCF₃ | H | H | Ph |
| 53 | O | CO | Me | H | H | H | OCF₃ | H | H | 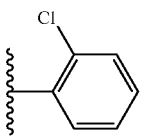 |
| 57 | O | CO | Me | H | H | H | OCF₃ | H | H | 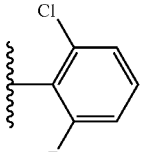 |
| 61 | CO | NH | Me | Ph | H | H | H | H | H | Ph |
| 63 | CO | NH | Me | H | H | H | H | H | H | Ph |
| 65 | CO | NH | Me | 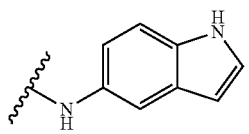 | H | H | Br | H | H | Ph |
| 67 | CO | NH | Me | —NHCH₃ | H | H | Br | H | H | Ph |
| 69 | CO | NH | Me | 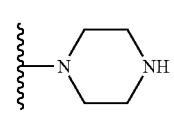 | H | H | Br | H | H | Ph |

-continued

| No. | A | B | R¹ | R² | R³ | R⁵ | R⁶ | R⁷ | R⁸ | R⁹ |
|---|---|---|---|---|---|---|---|---|---|---|
| 71 | CO | NH | Me | 3-hydroxyphenylamino | H | H | Br | H | H | Ph; and |
| 73 | CO | NH | Me | 2,3-dihydrobenzo[1,4]dioxin-6-ylamino | H | H | Br | H | H | Ph. |

12. The compound of claim 1 or claim 2 which inhibits mast cell or basophil cell degranulation with an $IC_{50}$ of about 20 μM or less as measured in an in vitro assay.

13. A pharmaceutical composition comprising a quinoline compound and a pharmaceutically acceptable excipient, carrier or diluent, said quinoline compound being a compound according to structural formula (I):

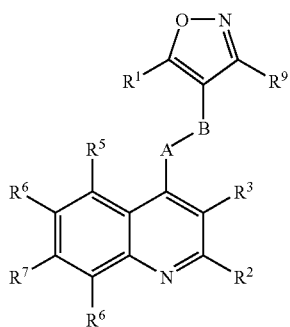

and a salt, hydrate, solvate or N-oxide thereof, wherein:
$R^1$ is an alkyl group optionally substituted with one or more of the same or different $R^{10}$ groups;
$R^2$, $R^3$, $R^5$, $R^6$, $R^7$ and $R^8$ are each, independently of one another, selected from the group consisting of a hydrogen atom, —$OR^d$, —$SR^d$, (C1-C3) haloalkyloxy, (C1-C3) perhaloalkyloxy, —$NR^c$-aryl, —$NR^c$-heteroaryl, halogen, (C1-C3) haloalkyl, (C1-C3) perhaloalkyl, —$CF_3$, —$CH_2CF_3$, —$CF_2CF_3$, (C1-C6) alkyl optionally substituted with one or more of the same or different $R^{10}$ groups, (C5-C10) aryl optionally substituted with one or more of the same or different $R^{10}$ groups, phenyl optionally substituted with one or more of the same or different $R^{10}$ groups, (and 5-10 membered heteroaryl optionally substituted with one or more of the same or different $R^{10}$ groups;
$R^9$ is selected from the group consisting of (C1-C3) haloalkyl, (C1-C3) perhaloalkyl, —$CF_3$, —$CH_2CF_3$, —$CF_2CF_3$, (C1-C6) alkyl optionally substituted with one or more of the same or different $R^{10}$ groups, (C5-C10) aryl optionally substituted with one or more of the same or different $R^{10}$ groups, phenyl optionally substituted with one or more of the same or different $R^{10}$ groups;
$R^{10}$ is selected from the group consisting of $R^a$, $R^b$, $R^a$ substituted with one or more of the same or different $R^a$ or $R^b$, —$OR^a$ substituted with one or more of the same or different $R^a$ or $R^b$, —$(CH_2)_m$—$R^b$, —$(CHR^a)_m$—$R^b$, —$O$—$(CH_2)_m$—$R^b$, —$S$—$(CH_2)_m$—$R^b$, and —$O$—$(CHR^a)_m$—$R^b$;

each $R^a$ is independently selected from the group consisting of hydrogen, (C1-C6) alkyl, (C3-C8) cycloalkyl, cyclohexyl, (C4-C11) cycloalkylalkyl, (C5-C10) aryl, phenyl, (C6-C16) arylalkyl, and benzyl;
each $R^b$ is a suitable group independently selected from the group consisting of —$OR^d$, (C1-C3) haloalkyloxy, halogen, and —$CF_3$,
each $R^c$ is independently a protecting group, $R^a$ or $R^a$ optionally substituted with one or more of the same or different $R^a$ or suitable $R^b$ groups;
each $R^d$ is independently a protecting group, $R^a$ or $R^a$ optionally substituted with one or more of the same or different $R^a$ or suitable $R^b$ groups;
each m is independently an integer from 1 to 3;
A is O, NH or CO; and
B is CO, NH or O, provided that one of A or B is CO.

14. The composition of claim 13 in which the quinoline compound is in the form of a pharmaceutically acceptable salt.

15. The composition of claim 14 in which the salt is a hydrochloride salt, a hydrogen sulfate salt, a sulfate salt or a phosphate salt.

16. The composition of claim 13 in which $R^1$ of the quinoline compound is methyl.

17. The composition of claim 16 in which $R^9$ of the quinoline compound is a substituted or unsubstituted phenyl.

18. The composition of claim 16 in which $R^9$ of the quinoline compound is a substituted phenyl.

19. The composition of claim 18 in which the substituted phenyl is 2-chlorophenyl or 2-chloro-6-fluorophenyl.

20. The composition of claim 13 in which $R^2$ is selected from the group consisting of hydrogen, phenyl, methyl, —$CO_2Et$, —$CF_3$, Cl, —$NHCH_3$,

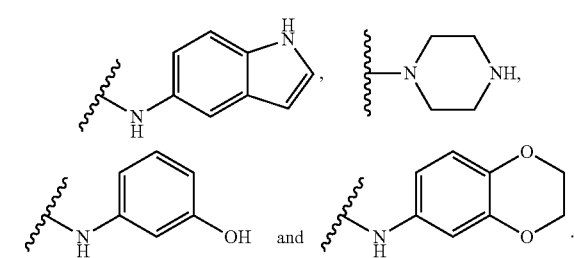

21. The composition of claim 13 in which $R^6$ of the quinoline compound is selected from the group consisting of hydrogen, F, —$OCF_3$ and Br.

22. The composition of claim 13 in which $R^7$ of the quinoline compound is selected from the group consisting of hydrogen, Cl and —$CF_3$.

23. The composition of claim 13 in which, in the quinoline compound,
R¹ is methyl;
R⁹ is a substituted or unsubstituted phenyl group;
R² is selected from the group consisting of hydrogen, phenyl, methyl, —CO₂Et, —CF₃, Cl, —NHCH₃,
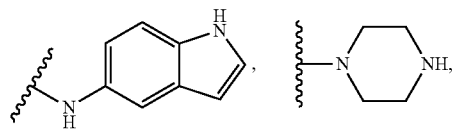
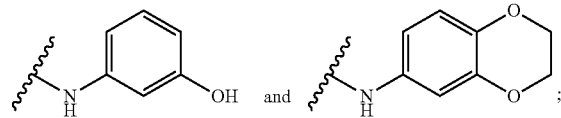
R⁶ is selected from the group consisting of hydrogen, F, —OCF₃ and Br; and
R⁷ is selected from the group consisting of hydrogen, Cl and —CF₃.
* * * * *

UNITED STATES PATENT AND TRADEMARK OFFICE
CERTIFICATE OF CORRECTION

PATENT NO. : 8,008,501 B2
APPLICATION NO. : 10/931481
DATED : August 30, 2011
INVENTOR(S) : Rajinder Singh and Hui Li It is certified that error appears in the above-identified patent and that said Letters Patent is hereby corrected as shown below:

In claim 1, column 45, line 22, please delete the text reading "and" and replace it with -- or --.

In claim 2, column 46, line 18, please delete the text reading "and" and replace it with -- or --.

In claim 11, column 48, line 35, please delete the text reading "and" and replace it with -- or --.

In claim 13, column 51, line 38, please delete the text reading "and" and replace it with -- or --.

Signed and Sealed this
Twenty-fifth Day of September, 2012

David J. Kappos
*Director of the United States Patent and Trademark Office*